US011468388B2

(12) United States Patent
Blahnik

(10) Patent No.: US 11,468,388 B2
(45) Date of Patent: Oct. 11, 2022

(54) FITNESS CHALLENGE E-AWARDS

(71) Applicant: Apple Inc., Cupertino, CA (US)

(72) Inventor: Jay Blahnik, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 102 days.

(21) Appl. No.: 17/020,188

(22) Filed: Sep. 14, 2020

(65) Prior Publication Data

US 2021/0103866 A1 Apr. 8, 2021

Related U.S. Application Data

(62) Division of application No. 14/871,516, filed on Sep. 30, 2015, now Pat. No. 10,776,739.

(60) Provisional application No. 62/057,869, filed on Sep. 30, 2014.

(51) Int. Cl.
*G06Q 10/06* (2012.01)
*G06Q 30/02* (2012.01)
*G16H 20/30* (2018.01)

(52) U.S. Cl.
CPC ..... *G06Q 10/0639* (2013.01); *G06Q 30/0207* (2013.01); *G16H 20/30* (2018.01)

(58) Field of Classification Search
CPC . G06Q 10/0639; G06Q 30/0207; G16H 20/30
See application file for complete search history.

(56) References Cited

U.S. PATENT DOCUMENTS

| 3,675,640 | A | 7/1972 | Gatts |
| 4,649,552 | A | 3/1987 | Yukawa |
| 4,907,795 | A | 3/1990 | Shaw et al. |
| 5,379,057 | A | 1/1995 | Clough et al. |

(Continued)

FOREIGN PATENT DOCUMENTS

| EP | 1462979 A1 | 9/2004 |
| EP | 1512370 B1 | 3/2005 |

(Continued)

OTHER PUBLICATIONS

"iPhone User Guide For iOS 7.1 Software", available online at retrieved on Aug. 10, 2015, 162 pages.

(Continued)

*Primary Examiner* — Robert J Utama
(74) *Attorney, Agent, or Firm* — Kilpatrick Townsend & Stockton LLP

(57) ABSTRACT

The present disclosure relates to systems and processes for users of electronic devices to issue physical activity goal challenges and rewards to one another. In one example, a first user can provide a physical activity goal that is to be performed by a second user. The first user can further provide a reward that is to be given to the second user in response to the second user completing the physical activity goal. An electronic device associated with the second user can be used to detect physical activity performed by the second user and to determine whether the second user has completed the physical activity goal. In response to determining that the second user has completed the physical activity goal, the reward can be issued to the second user. The reward can include an image, video, song, electronic message, amount of virtual currency, access to a service, or the like.

20 Claims, 17 Drawing Sheets

(56) References Cited

U.S. PATENT DOCUMENTS

| | | |
|---|---|---|
| 5,412,564 A | 5/1995 | Ecer |
| 5,434,913 A | 7/1995 | Tung et al. |
| 5,452,435 A | 9/1995 | Malouf et al. |
| 5,471,405 A | 11/1995 | Marsh |
| 5,489,249 A | 2/1996 | Brewer et al. |
| 5,490,247 A | 2/1996 | Tung et al. |
| 5,645,509 A | 7/1997 | Brewer et al. |
| 5,673,691 A | 10/1997 | Abrams et al. |
| 5,675,362 A | 10/1997 | Clough et al. |
| 5,788,655 A | 8/1998 | Yoshimura et al. |
| 5,794,018 A | 8/1998 | Vrvilo et al. |
| 5,819,735 A | 10/1998 | Mansfield et al. |
| 5,857,939 A | 1/1999 | Kaufman |
| 5,859,979 A | 1/1999 | Tung et al. |
| 5,890,995 A | 4/1999 | Bobick et al. |
| 5,890,997 A | 4/1999 | Roth |
| 5,913,062 A | 6/1999 | Vrvilo et al. |
| 5,954,640 A | 9/1999 | Szabo |
| 5,976,083 A | 11/1999 | Richardson et al. |
| 6,013,007 A | 1/2000 | Root et al. |
| 6,032,108 A | 2/2000 | Seiple et al. |
| 6,039,688 A | 3/2000 | Douglas et al. |
| 6,077,193 A | 6/2000 | Buhler et al. |
| 6,135,951 A | 10/2000 | Richardson et al. |
| 6,159,131 A | 12/2000 | Pfeffer |
| 6,323,846 B1 | 11/2001 | Westerman et al. |
| 6,357,147 B1 | 3/2002 | Darley et al. |
| 6,447,424 B1 | 9/2002 | Ashby et al. |
| 6,463,385 B1 | 10/2002 | Fry |
| 6,527,674 B1 | 3/2003 | Clem |
| 6,539,336 B1 | 3/2003 | Vock et al. |
| 6,553,037 B1 | 4/2003 | Pivowar et al. |
| 6,560,903 B1 | 5/2003 | Darley |
| 6,570,557 B1 | 5/2003 | Westerman et al. |
| 6,582,342 B2 | 6/2003 | Kaufman |
| 6,585,622 B1 | 7/2003 | Shum et al. |
| 6,587,127 B1 | 7/2003 | Leeke et al. |
| 6,619,835 B2 | 9/2003 | Kita |
| 6,623,427 B2 | 9/2003 | Mandigo |
| 6,662,023 B1 | 12/2003 | Helle |
| 6,677,932 B1 | 1/2004 | Westerman |
| 6,702,719 B1 | 3/2004 | Brown et al. |
| 6,716,139 B1 | 4/2004 | Hosseinzadeh-Dolkhani et al. |
| 6,725,281 B1 | 4/2004 | Zintel et al. |
| 6,735,568 B1 | 5/2004 | Buckwalter et al. |
| 6,749,537 B1 | 6/2004 | Hickman |
| 6,790,178 B1 | 9/2004 | Mault et al. |
| 6,793,607 B2 | 9/2004 | Neil |
| 6,808,473 B2 | 10/2004 | Hisano et al. |
| 6,898,550 B1 | 5/2005 | Blackadar et al. |
| 6,910,068 B2 | 6/2005 | Zintel et al. |
| 6,921,351 B1 | 7/2005 | Hickman et al. |
| 6,945,911 B2 | 9/2005 | Jackowski |
| 7,030,735 B2 | 4/2006 | Chen |
| 7,062,225 B2 | 6/2006 | White |
| 7,069,308 B2 | 6/2006 | Abrams |
| 7,070,539 B2 | 7/2006 | Brown et al. |
| 7,081,905 B1 | 7/2006 | Raghunath |
| 7,085,590 B2 | 8/2006 | Kennedy et al. |
| 7,130,664 B1 | 10/2006 | Williams |
| 7,171,331 B2 | 1/2007 | Vock et al. |
| 7,174,227 B2 | 2/2007 | Kobayashi et al. |
| 7,192,387 B2 | 3/2007 | Mendel |
| 7,200,517 B2 | 4/2007 | Darley et al. |
| 7,228,168 B2 | 6/2007 | Dardik et al. |
| 7,251,454 B2 | 7/2007 | White |
| 7,254,516 B2 | 8/2007 | Case, Jr. et al. |
| 7,261,690 B2 | 8/2007 | Teller et al. |
| 7,277,726 B2 | 10/2007 | Ahya et al. |
| 7,278,966 B2 | 10/2007 | Hjelt et al. |
| 7,292,867 B2 | 11/2007 | Werner et al. |
| 7,328,239 B1 | 2/2008 | Berberian et al. |
| 7,353,139 B1 | 4/2008 | Burrell et al. |
| 7,424,718 B2 | 9/2008 | Dutton |
| 7,454,002 B1 | 11/2008 | Gardner et al. |
| 7,496,277 B2 | 2/2009 | Ackley et al. |
| 7,519,327 B2 | 4/2009 | White |
| 7,523,040 B2 | 4/2009 | Kirchhoff et al. |
| 7,526,524 B2 | 4/2009 | White |
| 7,591,760 B2 | 9/2009 | Gordon et al. |
| 7,603,255 B2 | 10/2009 | Case, Jr. et al. |
| 7,614,008 B2 | 11/2009 | Ording |
| 7,618,345 B2 | 11/2009 | Corbalis et al. |
| 7,633,076 B2 | 12/2009 | Huppi et al. |
| 7,636,754 B2 | 12/2009 | Zhu et al. |
| 7,653,883 B2 | 1/2010 | Hotelling et al. |
| 7,656,824 B2 | 2/2010 | Wang et al. |
| 7,657,849 B2 | 2/2010 | Chaudhri et al. |
| 7,663,607 B2 | 2/2010 | Hotelling et al. |
| 7,670,263 B2 | 3/2010 | Ellis et al. |
| 7,683,252 B2 | 3/2010 | Oliver et al. |
| 7,753,825 B2 | 7/2010 | Jaquish et al. |
| 7,765,245 B2 | 7/2010 | Nichols et al. |
| 7,827,039 B2 | 11/2010 | Butcher et al. |
| 7,841,967 B1 | 11/2010 | Kahn et al. |
| 7,844,914 B2 | 11/2010 | Andre et al. |
| 7,946,959 B2 | 5/2011 | Shum et al. |
| 7,955,219 B2 | 6/2011 | Birrell et al. |
| 7,957,762 B2 | 6/2011 | Herz et al. |
| 7,973,231 B2 | 7/2011 | Bowen |
| 8,001,472 B2 | 8/2011 | Gilley et al. |
| 8,006,002 B2 | 8/2011 | Kalayjian et al. |
| 8,066,514 B2 | 11/2011 | Clarke |
| 8,095,120 B1 | 1/2012 | Blair et al. |
| 8,239,784 B2 | 8/2012 | Hotelling et al. |
| 8,279,180 B2 | 10/2012 | Hotelling et al. |
| 8,381,135 B2 | 2/2013 | Hotelling et al. |
| 8,479,122 B2 | 7/2013 | Hotelling et al. |
| 8,529,409 B1 | 9/2013 | Lesea-Ames |
| 8,543,081 B2 | 9/2013 | Scott et al. |
| 8,666,361 B2 | 3/2014 | Chu et al. |
| 8,910,299 B2 | 12/2014 | Michalske |
| 8,979,539 B1 | 3/2015 | Snyder |
| 9,020,538 B1 | 4/2015 | White et al. |
| 2001/0054180 A1 | 12/2001 | Atkinson |
| 2002/0007313 A1 | 1/2002 | Mai et al. |
| 2002/0015024 A1 | 2/2002 | Westerman et al. |
| 2002/0022551 A1 | 2/2002 | Watterson et al. |
| 2002/0022774 A1 | 2/2002 | Karnieli |
| 2002/0027164 A1 | 3/2002 | Mault et al. |
| 2002/0033753 A1 | 3/2002 | Imbo |
| 2002/0072932 A1 | 6/2002 | Swamy |
| 2002/0077784 A1 | 6/2002 | Vock et al. |
| 2002/0095460 A1 | 7/2002 | Benson |
| 2002/0107824 A1 | 8/2002 | Ahmed |
| 2002/0118121 A1 | 8/2002 | Lehrman et al. |
| 2003/0017914 A1 | 1/2003 | Jackowski |
| 2003/0028116 A1 | 2/2003 | Birnbaum |
| 2003/0059747 A1 | 3/2003 | Yoshida et al. |
| 2003/0097878 A1 | 5/2003 | Farringdon et al. |
| 2003/0175666 A1 | 9/2003 | Tanabe et al. |
| 2003/0204412 A1 | 10/2003 | Brier |
| 2003/0208113 A1 | 11/2003 | Mault et al. |
| 2003/0220971 A1 | 11/2003 | Kressin |
| 2003/0224337 A1 | 12/2003 | Shum et al. |
| 2003/0229900 A1 | 12/2003 | Reisman |
| 2004/0002041 A1 | 1/2004 | Peplinski et al. |
| 2004/0029684 A1 | 2/2004 | Zarif |
| 2004/0091843 A1 | 5/2004 | Albro et al. |
| 2004/0102931 A1 | 5/2004 | Ellis et al. |
| 2004/0106449 A1 | 6/2004 | Walker et al. |
| 2004/0107116 A1 | 6/2004 | Brown |
| 2004/0143673 A1 | 7/2004 | Kristjansson |
| 2004/0198555 A1 | 10/2004 | Anderson et al. |
| 2004/0201595 A1 | 10/2004 | Manchester |
| 2004/0220017 A1 | 11/2004 | Gordon et al. |
| 2004/0229729 A1 | 11/2004 | Albert et al. |
| 2005/0008993 A1 | 1/2005 | Bergh et al. |
| 2005/0008994 A1 | 1/2005 | Bisogno |
| 2005/0010638 A1 | 1/2005 | Richardson et al. |
| 2005/0014113 A1 | 1/2005 | Fleck et al. |
| 2005/0042582 A1 | 2/2005 | Graves |
| 2005/0044503 A1 | 2/2005 | Richardson et al. |
| 2005/0058970 A1 | 3/2005 | Perlman et al. |

(56) References Cited

U.S. PATENT DOCUMENTS

| | | |
|---|---|---|
| 2005/0060368 A1 | 3/2005 | Wang et al. |
| 2005/0070809 A1 | 3/2005 | Acres |
| 2005/0101314 A1 | 5/2005 | Levi |
| 2005/0107116 A1 | 5/2005 | Yamaguchi |
| 2005/0107216 A1 | 5/2005 | Lee et al. |
| 2005/0113649 A1 | 5/2005 | Bergantino |
| 2005/0125221 A1 | 6/2005 | Brown et al. |
| 2005/0125222 A1 | 6/2005 | Brown et al. |
| 2005/0125302 A1 | 6/2005 | Brown et al. |
| 2005/0164833 A1 | 7/2005 | Florio |
| 2005/0172311 A1 | 8/2005 | Hjelt et al. |
| 2005/0176461 A1 | 8/2005 | Bozzone et al. |
| 2005/0180341 A1 | 8/2005 | Nelson et al. |
| 2005/0190059 A1 | 9/2005 | Wehrenberg |
| 2005/0202934 A1 | 9/2005 | Olrik et al. |
| 2005/0209050 A1 | 9/2005 | Bartels |
| 2005/0226172 A1 | 10/2005 | Richardson et al. |
| 2005/0227811 A1 | 10/2005 | Shum et al. |
| 2005/0240705 A1 | 10/2005 | Novotney et al. |
| 2005/0266385 A1 | 12/2005 | Bisogno |
| 2005/0287499 A1 | 12/2005 | Yeager |
| 2005/0287502 A1 | 12/2005 | Southard et al. |
| 2006/0004862 A1 | 1/2006 | Fisher et al. |
| 2006/0017692 A1 | 1/2006 | Wehrenberg et al. |
| 2006/0025282 A1 | 2/2006 | Redmann |
| 2006/0026052 A1 | 2/2006 | Klett et al. |
| 2006/0026536 A1 | 2/2006 | Hotelling et al. |
| 2006/0033724 A1 | 2/2006 | Chaudhri et al. |
| 2006/0035200 A1 | 2/2006 | Pittman |
| 2006/0040244 A1 | 2/2006 | Kain |
| 2006/0047208 A1 | 3/2006 | Yoon |
| 2006/0052727 A1 | 3/2006 | Palestrant |
| 2006/0063980 A1 | 3/2006 | Hwang et al. |
| 2006/0085272 A1 | 4/2006 | Case et al. |
| 2006/0107822 A1 | 5/2006 | Bowen |
| 2006/0155578 A1 | 7/2006 | Eisenberger et al. |
| 2006/0173972 A1 | 8/2006 | Jung et al. |
| 2006/0197670 A1 | 9/2006 | Breibart |
| 2006/0197753 A1 | 9/2006 | Hotelling |
| 2006/0199155 A1 | 9/2006 | Mosher |
| 2006/0205564 A1 | 9/2006 | Peterson |
| 2006/0238517 A1 | 10/2006 | King et al. |
| 2006/0250524 A1 | 11/2006 | Roche |
| 2006/0253874 A1 | 11/2006 | Stark et al. |
| 2006/0256130 A1 | 11/2006 | Gonzalez |
| 2006/0263750 A1 | 11/2006 | Gordon |
| 2006/0293041 A1 | 12/2006 | Kim |
| 2007/0026999 A1 | 2/2007 | Merolle et al. |
| 2007/0032345 A1 | 2/2007 | Padmanabhan et al. |
| 2007/0033068 A1 | 2/2007 | Rao et al. |
| 2007/0033069 A1 | 2/2007 | Rao et al. |
| 2007/0059672 A1 | 3/2007 | Shaw |
| 2007/0074619 A1 | 4/2007 | Vergo |
| 2007/0087686 A1 | 4/2007 | Holm et al. |
| 2007/0100595 A1 | 5/2007 | Earles et al. |
| 2007/0110074 A1 | 5/2007 | Bradley et al. |
| 2007/0113726 A1 | 5/2007 | Oliver et al. |
| 2007/0130476 A1 | 6/2007 | Mohanty |
| 2007/0135043 A1 | 6/2007 | Hayes et al. |
| 2007/0135264 A1 | 6/2007 | Rosenberg |
| 2007/0136093 A1 | 6/2007 | Rankin et al. |
| 2007/0141540 A1 | 6/2007 | Borg |
| 2007/0166683 A1 | 7/2007 | Chang et al. |
| 2007/0192106 A1 | 8/2007 | Zilca |
| 2007/0219059 A1 | 9/2007 | Schwartz et al. |
| 2007/0265138 A1 | 11/2007 | Ashby |
| 2007/0287596 A1 | 12/2007 | Case et al. |
| 2007/0287597 A1 | 12/2007 | Cameron |
| 2008/0015422 A1 | 1/2008 | Wessel |
| 2008/0033827 A1 | 2/2008 | Kuang et al. |
| 2008/0077489 A1 | 3/2008 | Gilley et al. |
| 2008/0096726 A1 | 4/2008 | Riley et al. |
| 2008/0150731 A1 | 6/2008 | Laukkanen et al. |
| 2008/0155470 A1 | 6/2008 | Khedouri et al. |
| 2008/0177860 A1 | 7/2008 | Khedouri et al. |
| 2008/0195594 A1 | 8/2008 | Gerjets et al. |
| 2008/0195997 A1 | 8/2008 | Herberger et al. |
| 2008/0215968 A1 | 9/2008 | Bekerman |
| 2008/0242521 A1 | 10/2008 | Einav |
| 2008/0258917 A1 | 10/2008 | Boyd et al. |
| 2008/0320391 A1 | 12/2008 | Lemay et al. |
| 2009/0047645 A1 | 2/2009 | Dibenedetto et al. |
| 2009/0087819 A1 | 4/2009 | Adachi et al. |
| 2009/0169171 A1 | 7/2009 | Massey et al. |
| 2009/0199130 A1 | 8/2009 | Tsern et al. |
| 2009/0205041 A1 | 8/2009 | Michalske |
| 2009/0312105 A1 | 12/2009 | Koplar |
| 2009/0327894 A1 | 12/2009 | Rakib et al. |
| 2010/0079291 A1 | 4/2010 | Kroll et al. |
| 2010/0081116 A1 | 4/2010 | Barasch et al. |
| 2010/0198687 A1 | 8/2010 | Bang et al. |
| 2011/0003665 A1 | 1/2011 | Burton et al. |
| 2011/0088086 A1 | 4/2011 | Swink et al. |
| 2011/0098928 A1 | 4/2011 | Hoffman et al. |
| 2011/0137678 A1 | 6/2011 | Williams |
| 2011/0137836 A1 | 6/2011 | Kuriyama et al. |
| 2011/0230986 A1 | 9/2011 | Lafortune et al. |
| 2011/0246509 A1 | 10/2011 | Migita et al. |
| 2011/0261079 A1 | 10/2011 | Ingrassia, Jr. et al. |
| 2012/0041767 A1 | 2/2012 | Hoffman et al. |
| 2012/0116550 A1 | 5/2012 | Hoffman et al. |
| 2012/0185905 A1 | 7/2012 | Kelley |
| 2012/0198317 A1 | 8/2012 | Eppolito et al. |
| 2012/0230510 A1 | 9/2012 | Dinescu et al. |
| 2012/0253485 A1 | 10/2012 | Weast et al. |
| 2012/0258684 A1 | 10/2012 | Franz et al. |
| 2012/0326873 A1 | 12/2012 | Utter |
| 2013/0017891 A1 | 1/2013 | Romero et al. |
| 2013/0024880 A1 | 1/2013 | Moloney-Egnatios et al. |
| 2013/0106603 A1 | 5/2013 | Weast et al. |
| 2013/0106684 A1 | 5/2013 | Weast et al. |
| 2013/0132028 A1 | 5/2013 | Crankson et al. |
| 2013/0143512 A1 | 6/2013 | Hernandez et al. |
| 2013/0184613 A1 | 7/2013 | Homsi et al. |
| 2013/0188322 A1 | 7/2013 | Lowe |
| 2013/0197679 A1 | 8/2013 | Balakrishnan et al. |
| 2013/0203475 A1 | 8/2013 | Kil et al. |
| 2013/0225118 A1 | 8/2013 | Jang et al. |
| 2013/0262155 A1 | 10/2013 | HinKamp |
| 2013/0290013 A1 | 10/2013 | Forrester |
| 2013/0295872 A1 | 11/2013 | Guday et al. |
| 2013/0325394 A1 | 12/2013 | Yuen et al. |
| 2013/0325396 A1 | 12/2013 | Yuen et al. |
| 2013/0330694 A1* | 12/2013 | Watterson ............ G09B 19/00 434/247 |
| 2014/0065588 A1 | 3/2014 | Jacobson et al. |
| 2014/0081666 A1 | 3/2014 | Teller et al. |
| 2014/0122601 A1 | 5/2014 | Poston et al. |
| 2014/0139637 A1 | 5/2014 | Mistry et al. |
| 2014/0199966 A1 | 7/2014 | Schushan |
| 2014/0218369 A1 | 8/2014 | Yuen et al. |
| 2014/0239065 A1 | 8/2014 | Zhou et al. |
| 2014/0240122 A1 | 8/2014 | Roberts et al. |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0272894 A1 | 9/2014 | Grimes et al. |
| 2014/0282153 A1 | 9/2014 | Christiansen et al. |
| 2014/0285312 A1 | 9/2014 | Laaksonen et al. |
| 2014/0328571 A1 | 11/2014 | Roberts, Jr. et al. |
| 2014/0337451 A1 | 11/2014 | Choudhary et al. |
| 2014/0344723 A1 | 11/2014 | Malik et al. |
| 2015/0052618 A1 | 2/2015 | Michalske |
| 2015/0057943 A1 | 2/2015 | Self et al. |
| 2015/0086174 A1 | 3/2015 | Abecassis et al. |
| 2015/0106025 A1 | 4/2015 | Keller et al. |
| 2015/0130830 A1 | 5/2015 | Nagasaki et al. |
| 2015/0196836 A1 | 7/2015 | Drendel |
| 2015/0341410 A1 | 11/2015 | Schrempp et al. |
| 2015/0347711 A1 | 12/2015 | Soli et al. |
| 2015/0350861 A1 | 12/2015 | Soli et al. |
| 2016/0019360 A1 | 1/2016 | Pahwa et al. |

(56) References Cited

U.S. PATENT DOCUMENTS

| | | | |
|---|---|---|---|
| 2016/0058336 A1 | 3/2016 | Blahnik et al. | |
| 2016/0058337 A1 | 3/2016 | Blahnik et al. | |
| 2017/0053542 A1 | 2/2017 | Wilson et al. | |

FOREIGN PATENT DOCUMENTS

| | | | |
|---|---|---|---|
| EP | 1585014 A2 | 10/2005 | |
| EP | 2025368 A3 | 2/2009 | |
| GB | 2253706 B | 9/1992 | |
| GB | 2284060 A | 5/1995 | |
| GB | 2409040 A | 6/2005 | |
| JP | 06-187118 | 7/1994 | |
| JP | 2001-76078 | 3/2001 | |
| JP | 2003-337863 A | 11/2003 | |
| JP | 2004-102609 A | 4/2004 | |
| JP | 2006-230679 A | 9/2006 | |
| JP | 2007-013228 A | 1/2007 | |
| JP | 2008-183339 A | 8/2008 | |
| JP | 2011-125633 A | 6/2011 | |
| JP | 2011-192126 A | 9/2011 | |
| KR | 1999-0073234 A | 10/1999 | |
| TW | 201210368 A | 3/2012 | |
| TW | 201240499 A | 10/2012 | |
| WO | 97/14357 | 4/1997 | |
| WO | 99/41682 A2 | 8/1999 | |
| WO | 00/52604 | 9/2000 | |
| WO | 01/16855 | 3/2001 | |
| WO | 01/65460 | 9/2001 | |
| WO | 02/15986 | 2/2002 | |
| WO | 02/062425 | 8/2002 | |
| WO | 02/093272 | 11/2002 | |
| WO | 2005/032363 | 4/2005 | |
| WO | 2005/036918 A1 | 4/2005 | |
| WO | 2005/070289 A1 | 8/2005 | |
| WO | 2005/082472 A1 | 9/2005 | |
| WO | 2005/093633 A2 | 10/2005 | |
| WO | 2005/087323 A3 | 3/2006 | |
| WO | 2006/042415 A1 | 4/2006 | |
| WO | 2006/079942 | 8/2006 | |
| WO | 20070/99206 A1 | 9/2007 | |
| WO | 2012/078079 A2 | 6/2012 | |

OTHER PUBLICATIONS

"Microsoft Zune Impressions—Part 1," DigitalArts Online Magazine, Dec. 4, 2006, 6 pages.

"Notice from the European Patent Office dated Oct. 1, 2007 concerning business methods." Official Journal of the European Patent Office, vol. 30, No. 7, Nov. 1, 2007, 2 pages.

"Statement in Accordance With the Notice From the European Patent Office dated Oct. 1, 2007 Concerning Business Methods." Official Journal of the European Patent Office, Nov. 1, 2007, 1 page.

"Podfitness Delivers On myMedia Promise," Utah Tech Jobs.com, Nov. 13, 2006, 4 pages.

Advisory Action received for U.S. Appl. No. 14/839,922, dated Mar. 24, 2017, 4 pages.

Creative NOMAD® Digital Audio Player User Guide, Jun. 1999. Title page (1 page), publication information page (1 page), software license agreement (2 pages), table of contents (2 pages), introduction pages (2 pages), and pp. 1-34.

Creative NOMAD® II Getting Started Guide, Jan. 2000. Title page (1 page), publication information page (1 page), software license agreement (2 pages), safety information (1 page), table of contents (2 pages), introduction (2 pages), and pp. 1-38.

Ericsson Inc. "Cellular Phone With Integrated MP3 Player." Research Disclosure Journal No. 41815, Research Disclosure Database No. 418015 (Feb. 1999), 2 pages.

Final Office Action received for U.S. Appl. No. 14/599,425, dated May 19, 2017, 24 pages.

Final Office Action received for U.S. Appl. No. 14/599,425, dated Oct. 8, 2015, 20 pages.

Final Office Action received for U.S. Appl. No. 14/839,922, dated Dec. 14, 2016, 22 pages.

Intention to Grant received for Danish Patent Application No. PA201570668, dated Mar. 27, 2017, 2 pages.

International Preliminary Report on Patentability received for PCT Patent Application No. PCT/US2015/047282, dated Mar. 16, 2017, 26 pages.

International Preliminary Report on Patentability received for PCT Patent Application No. PCT/US2013/073195, dated Jun. 7, 2016, 9 pages.

International Preliminary Report on Patentability received for PCT Patent Application No. PCT/US2015/032474, dated Dec. 15, 2016, 7 pages.

International Search Report and Written Opinion received for PCT Patent Application No. PCT/US2015/032474, dated Aug. 19, 2015, 8 pages.

International Search Report and Written Opinion received for PCT Patent Application No. PCT/US2015/047282, dated May 9, 2016, 33 pages.

International Search Report and Written Opinion received for PCT Patent Application No. PCT/US2016/037686, dated Sep. 9, 2016, 19 pages.

International Search Report received for PCT Patent Application No. PCT/US2013/073195, dated Jun. 23, 2014, 3 pages.

Invitation to Pay Additional Fees received for PCT Patent Application No. PCT/US2015047282, mailed on Dec. 22, 2015, 7 pages.

Kamijo, Noboru, "Next Generation Mobile System—WatchPad1. 5", available at , retrieved on Jul. 4, 2015, 2 pages.

MENTA. "1200 Song MP3 Portable is a Milestone Player." http://www.mp3newswire.nel/stories/personaljuke.html. Jan. 11, 2000. 4 pages.

Non Final Office Action received for U.S. Appl. No. 14/839,916, dated Feb. 4, 2016, 19 pages.

Non Final Office Action received for U.S. Appl. No. 14/839,922, dated Feb. 25, 2016, 20 pages.

Non-Final Office Action received for U.S. Appl. No. 14/503,372, dated Dec. 5, 2014, 11 pages.

Non-Final Office Action received for U.S. Appl. No. 14/599,425, dated Mar. 17, 2015, 16 pages.

Non-Final Office Action received for U.S. Appl. No. 14/599,425, dated Oct. 26, 2016, 22 pages.

Non-Final Office Action received for U.S. Appl. No. 14/839,916, dated May 1, 2017, 18 pages.

Non-Final Office Action received for U.S. Appl. No. 14/839,922, dated Aug. 17, 2016, 25 pages.

Notice of Allowance received for Chinese Patent Application No. 201520358505.5, dated Jan. 13, 2016, 3 pages (2 pages of English Translation and 1 page of Official Copy).

Notice of Allowance received for Danish Patent Application No. PA201570666, dated Sep. 15, 2016, 1 page.

Notice of Allowance received for Korean Patent Application No. 10-2016-7033638, dated May 31, 2017, 5 pages (2 pages of English Translation and 3 pages of Official Copy).

Notice of Allowance received for Taiwanese Patent Application No. 104117509, dated Mar. 31, 2017, 3 pages (see attached 37 CFR § 1.98(a) (3)).

Notice of Allowance received for Taiwanese Patent Application No. 104128685, dated May 3, 2017, 3 pages (see attached 37 CFR § 1.98(a) (3)).

Notice of Allowance received for U.S. Appl. No. 14/839,916, dated Aug. 31, 2016, 11 pages.

Notice of Allowance received for U.S. Appl. No. 14/839,922, dated Jul. 6, 2017, 8 pages.

Office Action received for Australian Patent Application No. 2015100734, dated Jul. 29, 2015, 5 pages.

Office Action received for Australian Patent Application No. 2015267240, dated Apr. 10, 2017, 5 pages.

Office Action received for Australian Patent Application No. 2015312215, dated Oct. 13, 2016, 3 pages.

Office Action received for Danish Patent Application No. PA201570666, dated Feb. 2, 2016, 9 pages.

Office Action received for Danish Patent Application No. PA201570666, dated Jun. 27, 2016, 4 pages.

(56) References Cited

OTHER PUBLICATIONS

Office Action received for Danish Patent Application No. PA201570668, dated Apr. 8, 2016, 8 pages.
Office Action received for Danish Patent Application No. PA201570668, dated Sep. 9, 2016, 3 pages.
Office Action received for Danish Patent Application No. PA201670656, dated Jun. 14, 2017, 3 pages.
Office Action Received for Danish Patent Application No. PA201670656, dated Nov. 3, 2016, 8 pages.
Office Action received for Japanese Patent Application No. 2016535045, dated May 12, 2017, 10 pages (5 pages of English Translation and 5 pages of Official Copy).
Office Action received for Korean Patent Application No. 10-2016-7033638, dated Jan. 31, 2017, 6 pages (2 pages of English Translation and 4 pages of Official Copy).
Office Action received for Taiwanese Patent Application No. 104117509, dated Aug. 22, 2016, 6 pages (3 pages of English Translation and 3 pages of Official Copy).
Office Action received for Taiwanese Patent Application No. 104128685, dated Jan. 4, 2017, 40 pages (15 pages of English Translation and 25 pages of Official Copy).
Oliver et al. "Enhancing Exercise Performance through Real-time Physiological Monitoring and Music: A User Study." Pervasive Health Conference and Workshops, pp. 1-10 (2007).
Pike, Weight Watchers On-the-Go, Apr. 12, 2005, PC Magazine, vol. 24, Iss.6; p. 149.
Reinventing the Scroll Wheel, CNET news.com, Aug. 22, 2006, 16 pages: <http://www.news.com/2300-1041_3-6107951-1.html?tag=ne.gall.pg; http://www.news.com/2300-1041_3-6107951-2.html?tag=ne.gall.oghttp://www.news.com/2300-1041_3-6107951-3.html?tag=ne.gall.pghttp://www.news.com/2300-1041_3-6107951-4.html?tag=ne.gall.pg.
Rio 500 Getting Started Guide, 1999. 2 pages.
Rio PMP300 User's Guide (1998). Title page (1 page), copyright notices (1 page), table of contents (2 pages), and pp. 1-24).
Search Report and Opinion received for Danish Patent Application No. PA201770191, dated Jun. 30, 2017, 9 pages.
Sensei.com, Feb. 10, 2008, 1 page.
Written Opinion received for PCT Patent Application No. PCT/US2013/073195, dated Jun. 23, 2014, 8 pages.

\* cited by examiner

FITNESS CHALLENGE E-AWARDS

CROSS-REFERENCE TO RELATED APPLICATION

This application is a divisional of U.S. patent application Ser. No. 14/871,516, filed on Sep. 30, 2015 (now U.S. Pat. No. 10,776,739), which claims the benefit of priority of U.S. Provisional Patent Application No. 62/057,869, filed on Sep. 30, 2014, each of which is hereby incorporated by reference in its entirety for all purposes.

FIELD

The following disclosure relates generally to electronic devices for monitoring a user's physical activity and, more specifically, to providing rewards to users for physical activity tracked using an electronic device.

BACKGROUND

Approximately 133 million Americans currently suffer from at least one chronic health condition. This number is expected to rise to approximately 165 million by the year 2020. This deterioration in health can be attributed largely to a sedentary lifestyle with little to no physical activity. For example, lack of sufficient physical activity can increase the risk of developing diabetes, hypertension, colon cancer, depression and anxiety, obesity, and weak muscles and bones. In addition, recent studies have found that extended periods of inactivity (e.g., sitting at a desk), can lead to serious health risks, such as an increased risk of a heart attack.

To improve the health of individuals, tools for monitoring a user's health and physical activity have been developed. For example, activity monitors can track an individual's physical activity using a variety of metrics including steps taken, elevation climbed, distance travelled, calories burned, or the like. While these monitors can track the amount of physical activity performed by a user, they fail to positively motivate users to engage in physical activity.

SUMMARY

In some embodiments, a non-transitory computer readable storage medium stores one or more programs, the one or more programs comprising instructions, which when executed by an electronic device having one or more processors, cause the electronic device to: receive a physical activity goal challenge communication including a reward in an unreleased state; store the reward in the unreleased state, wherein access to the reward is restricted while in the unreleased state; receive activity data generated using an activity sensor of the electronic device, wherein the activity data is representative of user movement associated with the electronic device that is detected by the activity sensor; determine, based on the activity data, whether a physical activity goal has been completed; and in response to determining that the physical activity goal has been completed, change the state of the reward to a released state, wherein access to the reward is allowed while in the released state.

In some embodiments, a method comprises, at an electronic device: receiving a physical activity goal challenge communication including a reward in an unreleased state; storing the reward in the unreleased state, wherein access to the reward is restricted while in the unreleased state; receiving activity data generated by an activity sensor of the electronic device, wherein the activity data is representative of user movement associated with the electronic device that is detected by the activity sensor; determining, based on the activity data, whether a physical activity goal has been completed; and in response to determining that the physical activity goal has been completed, changing the state of the reward to a released state, wherein access to the reward is allowed while in the released state.

In some embodiments, an electronic device comprises a display; one or more processors; a memory; and one or more programs, wherein the one or more programs are stored in memory and configured to be executed by the one or more processors, the one or more programs including instructions for: receiving a physical activity goal challenge communication including a reward in an unreleased state and a physical activity goal; storing the reward in the unreleased state, wherein access to the reward is restricted while in the unreleased state; receiving activity data generated by an activity sensor of the electronic device, wherein the activity data is representative of user movement associated with the electronic device that is detected by the activity sensor; determining, based on the activity data, whether the physical activity goal has been completed; and in response to determining that the physical activity goal has been completed, changing the state of the reward to a released state, wherein access to the reward is allowed while in the released state.

In some embodiments, a non-transitory computer readable storage medium stores one or more programs, the one or more programs comprising instructions, which when executed by an electronic device having one or more processors, cause the electronic device to: receive a physical activity goal challenge communication including a physical activity goal; receive activity data generated by an activity sensor of the electronic device, wherein the activity data is representative of user movement associated with the electronic device that is detected by the activity sensor; determine, based on the activity data, whether the physical activity goal has been completed; and in response to determining that the physical activity goal has been completed: transmit, to one or more servers, a notification that the physical activity goal has been completed; receive a reward; and store the reward in a released state, wherein access to the reward is allowed while in the released state.

In some embodiments, a method comprising: at one or more processors of an electronic device: receiving a physical activity goal challenge communication including a physical activity goal; receiving activity data generated by an activity sensor of the electronic device, wherein the activity data is representative of user movement associated with the electronic device that is detected by the activity sensor; determining, based on the activity data, whether the physical activity goal has been completed; and in response to determining that the physical activity goal has been completed: transmitting, to one or more servers, a notification that the physical activity goal has been completed; receiving a reward; and storing the reward in a released state, wherein access to the reward is allowed while in the released state.

In some embodiments, an electronic device comprises a display; one or more processors; a memory; and one or more programs, wherein the one or more programs are stored in memory and configured to be executed by the one or more processors, the one or more programs including instructions for: receiving a physical activity goal challenge communication including a physical activity goal; receiving activity data generated by an activity sensor of the electronic device, wherein the activity data is representative of user movement associated with the electronic device that is detected by the activity sensor; determining, based on the activity data, whether the physical activity goal has been completed; and in response to determining that the physical activity goal has been completed: transmitting, to one or more servers, a notification that the physical activity goal has been completed; receiving a reward; and storing the reward in a released state, wherein access to the reward is allowed while in the released state.

DETAILED DESCRIPTION

In the following description of the disclosure and examples, reference is made to the accompanying drawings in which it is shown by way of illustration specific examples that can be practiced. It is to be understood that other examples can be practiced and structural changes can be made without departing from the scope of the disclosure.

Electronic Devices

Figure 2:
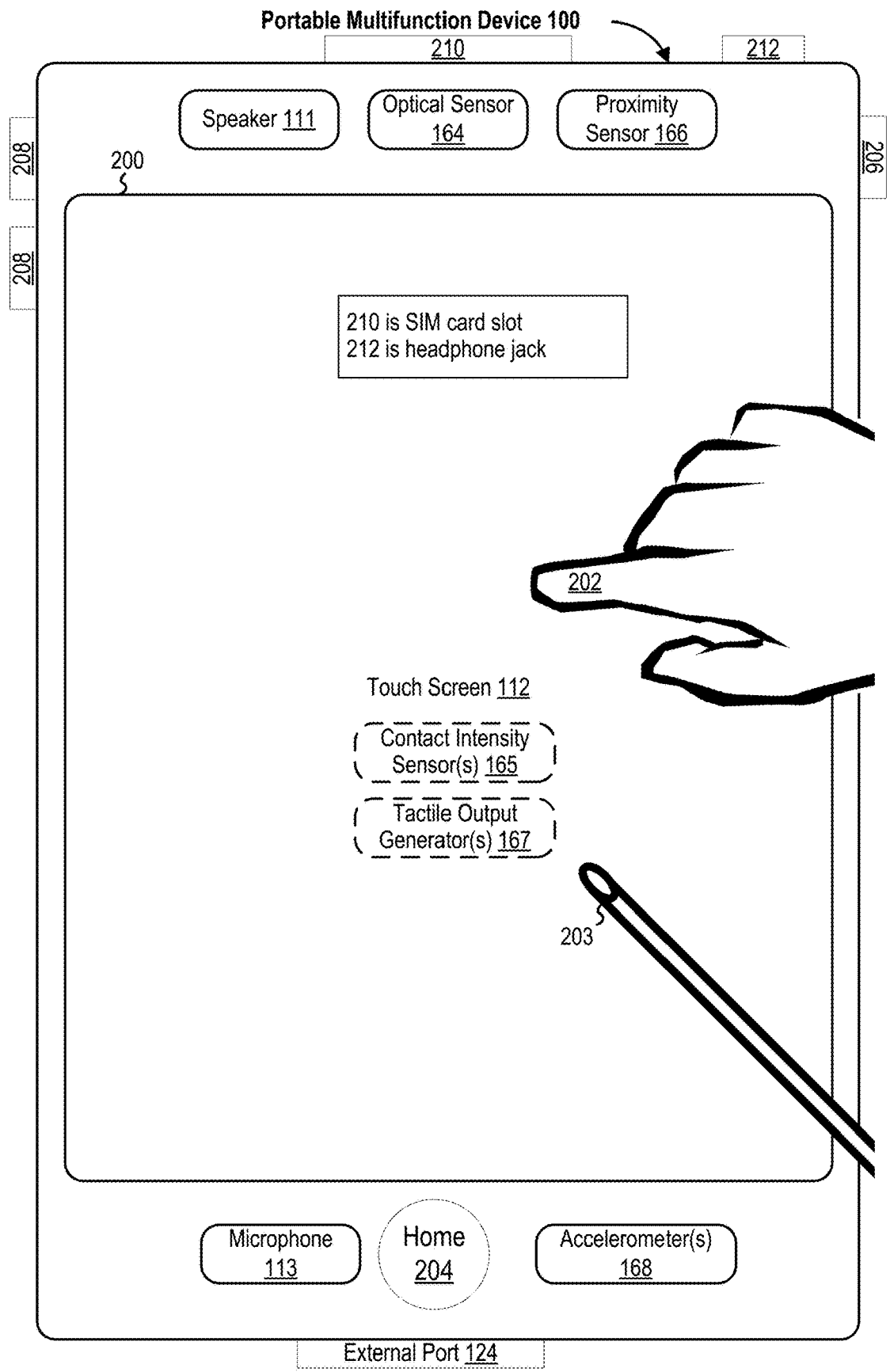
FIG. 2 illustrates a portable multifunction device having a touch screen in accordance with some examples.
Figure 3:
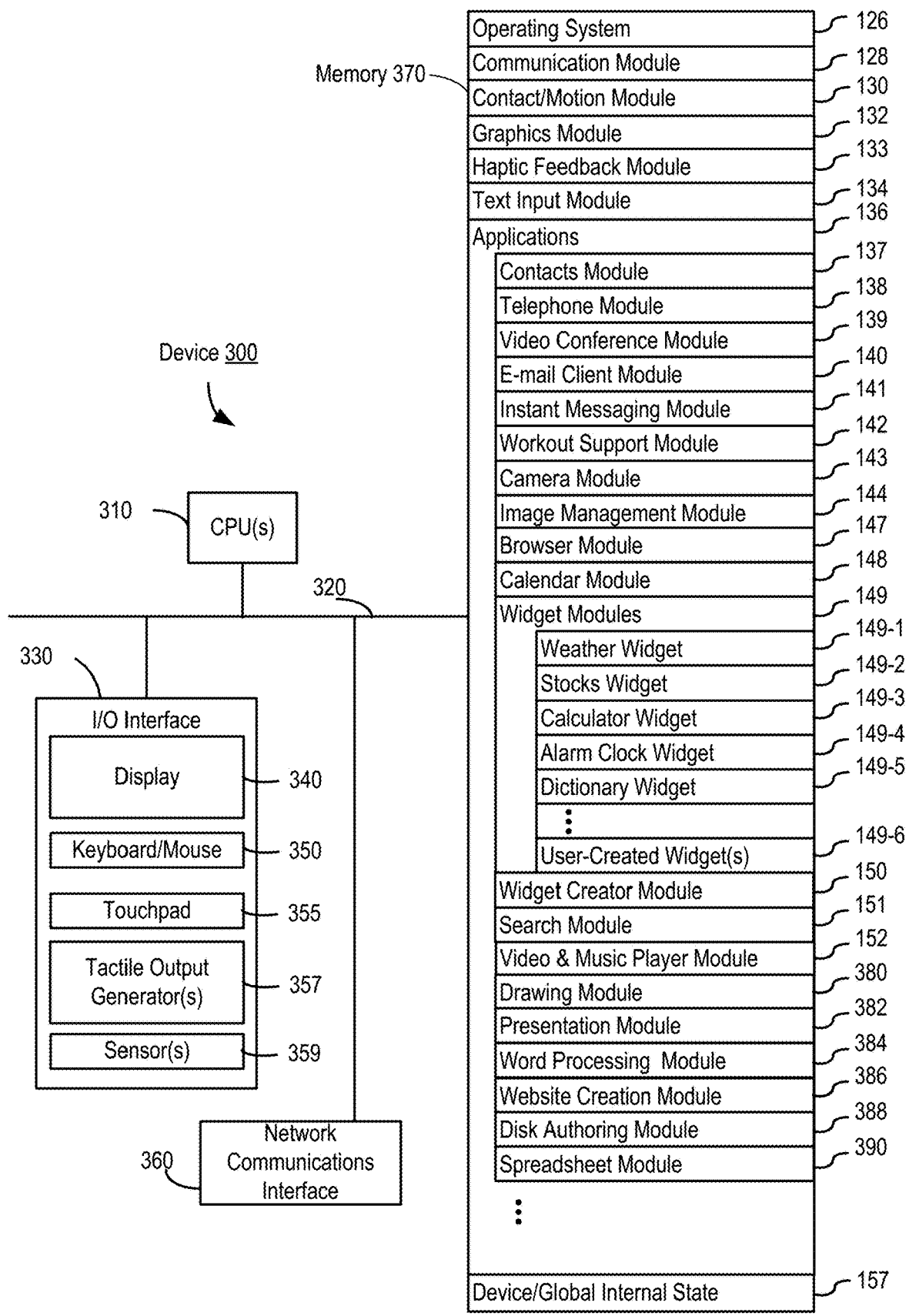
FIG. 3 is a block diagram of an exemplary multifunction device with a display and a touch-sensitive surface in accordance with some examples.
Figure 4A:
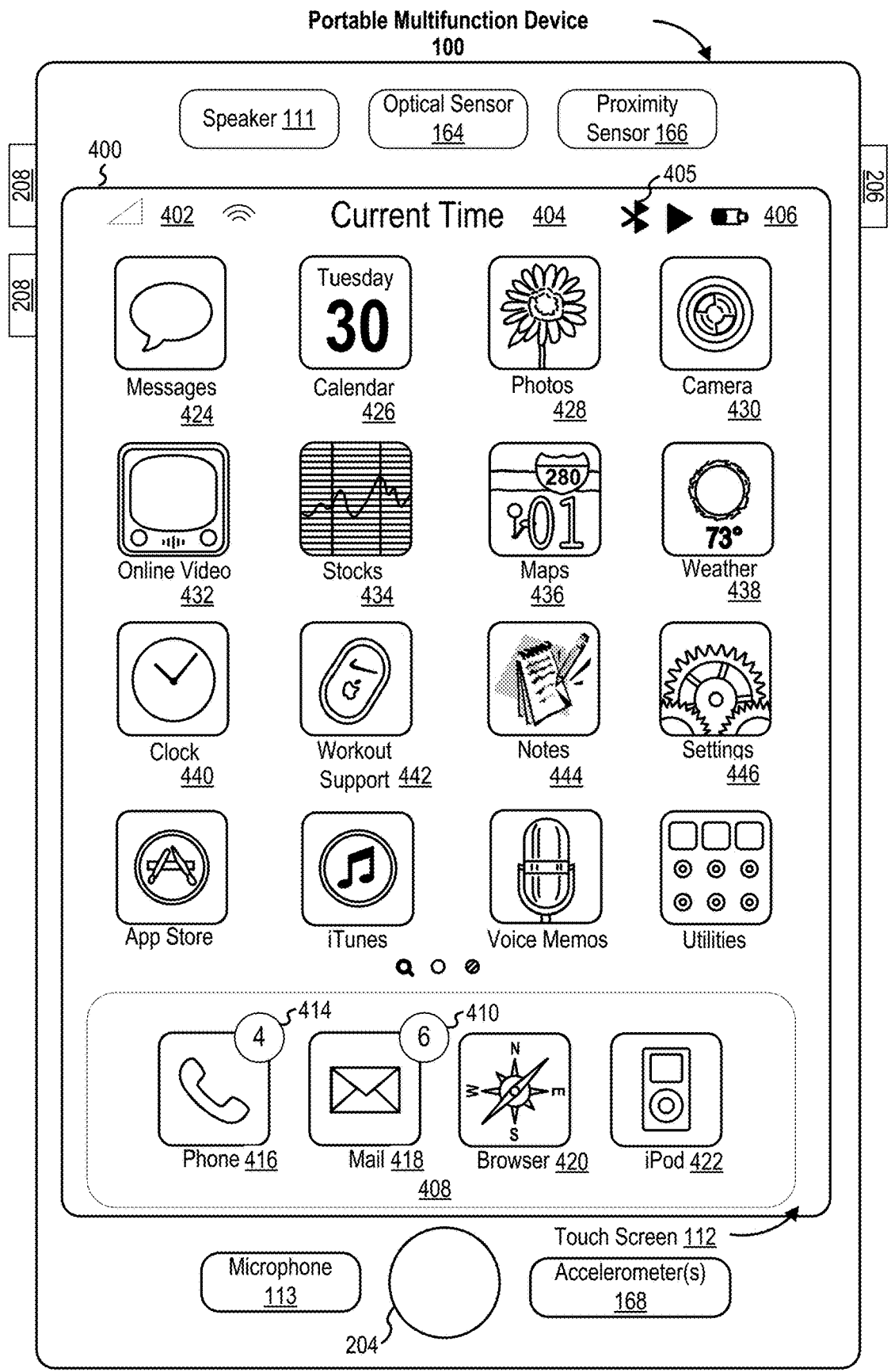
FIG. 4A illustrates an exemplary user interface for a menu of applications on a portable multifunction device in accordance with some examples.
Figure 4B:
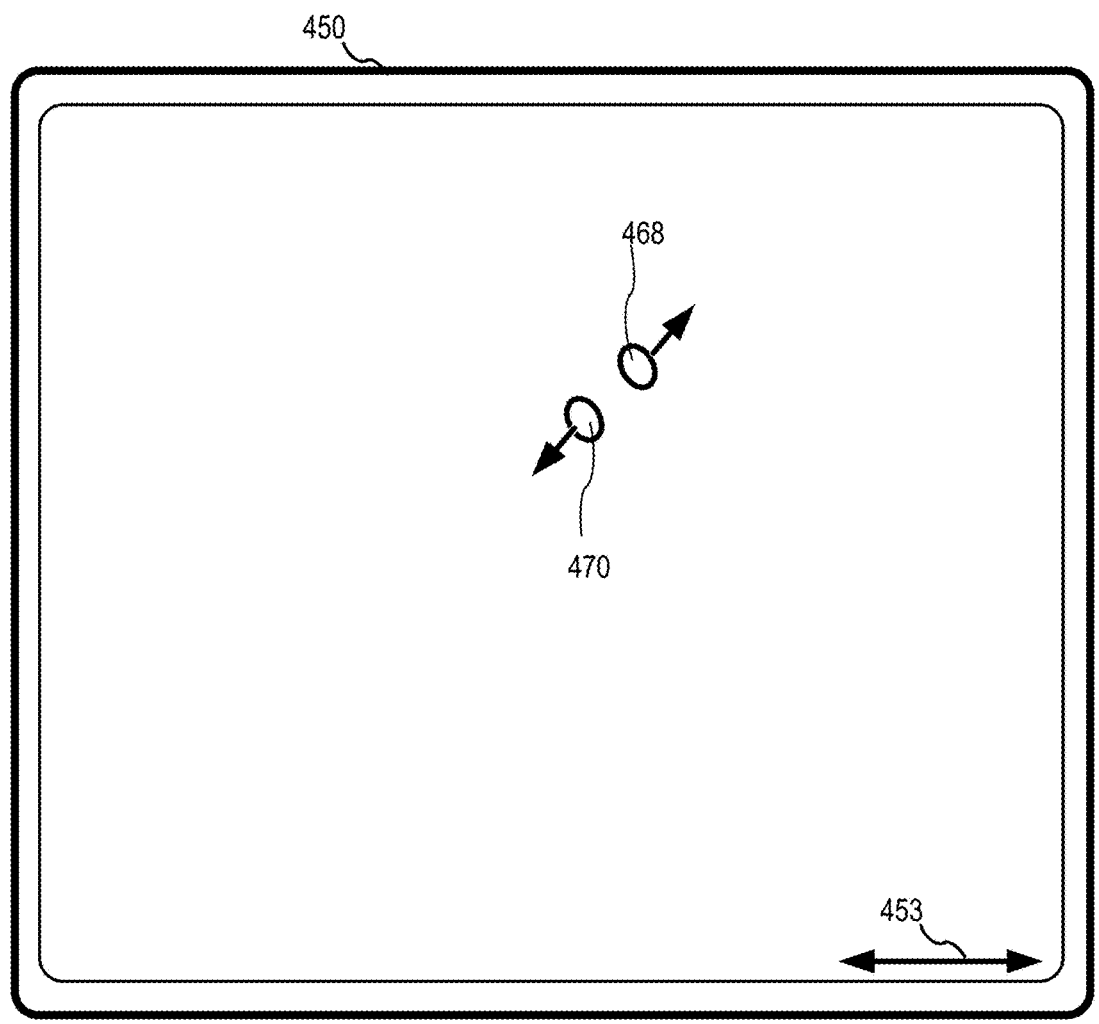
FIG. 4B illustrates an exemplary user interface for a multifunction device with a touch-sensitive surface that is separate from the display in accordance with some examples.
Figure 4B:
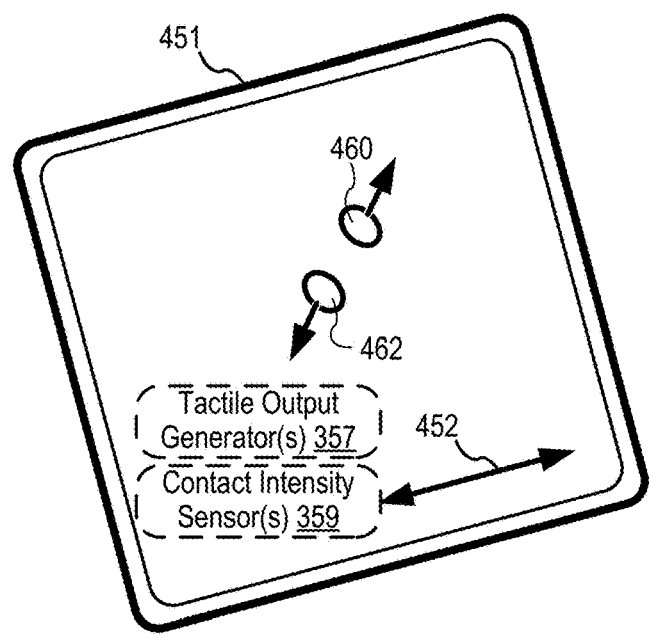

FIGS. 1A-1B, 2, 3, and 5A-B illustrate exemplary devices for providing rewards to user for performing physical activity. FIGS. 4A-4B illustrate exemplary user interfaces that can be displayed on these exemplary devices.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a", "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, Calif. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
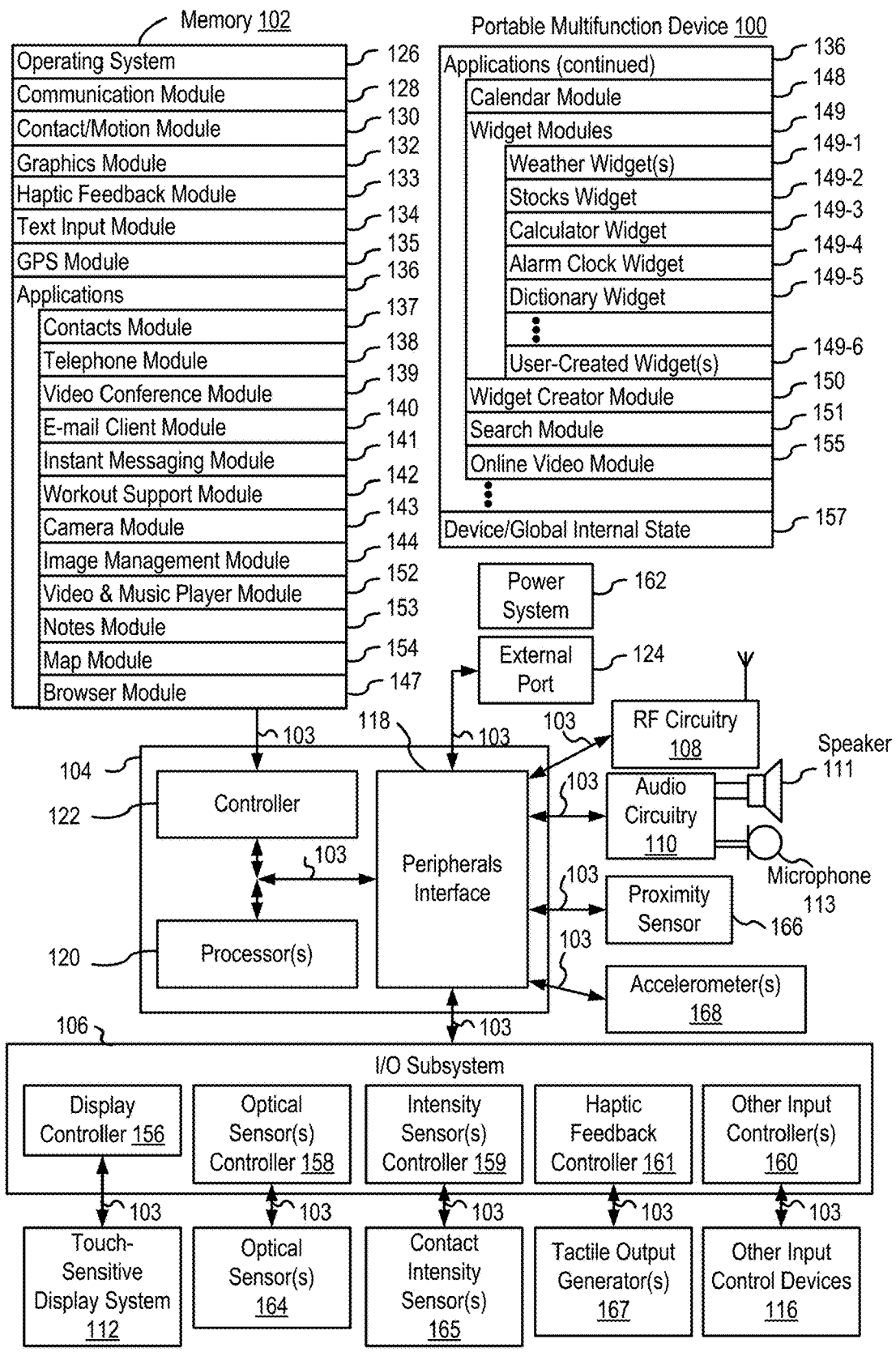
FIG. 1A is a block diagram illustrating a portable multifunction device with a touch-sensitive display in accordance with some examples.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes one or more computer-readable storage mediums. The computer-readable storage mediums are optionally tangible and non-transitory. The computer-readable storage mediums are optionally transitory. Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, Calif.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112 which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIRE-WIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with the 30-pin connector used on iPod® (trademark of Apple Inc.) devices.

Contact/motion module 130 optionally detects contact with touch screen 112 (in conjunction with display controller 156) and other touch sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact) determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast or other visual property) of graphics that are displayed. As used herein, the term "graphics" includes any object that can be displayed to a user, including without limitation text, web pages, icons (such as user-interface objects including soft keys), digital images, videos, animations and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts 137, e-mail 140, IM 141, browser 147, and any other application that needs text input).

GPS module 135 determines the location of the device and provides this information for use in various applications (e.g., to telephone 138 for use in location-based dialing, to camera 143 as picture/video metadata, and to applications that provide location-based services such as weather widgets, local yellow page widgets, and map/navigation widgets).

Applications 136 optionally include the following modules (or sets of instructions), or a subset or superset thereof:
  Contacts module 137 (sometimes called an address book or contact list);
  Telephone module 138;
  Video conferencing module 139;
  E-mail client module 140;
  Instant messaging (IM) module 141;
  Workout support module 142;
  Camera module 143 for still and/or video images;
  Image management module 144;
  Video player module;
  Music player module;
  Browser module 147;
  Calendar module 148;
  Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
  Widget creator module 150 for making user-created widgets 149-6;
  Search module 151;
  Video and music player module 152, which merges video player module and music player module;
  Notes module 153;
  Map module 154; and/or
  Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone 138, video conference module 139, e-mail 140, or IM 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
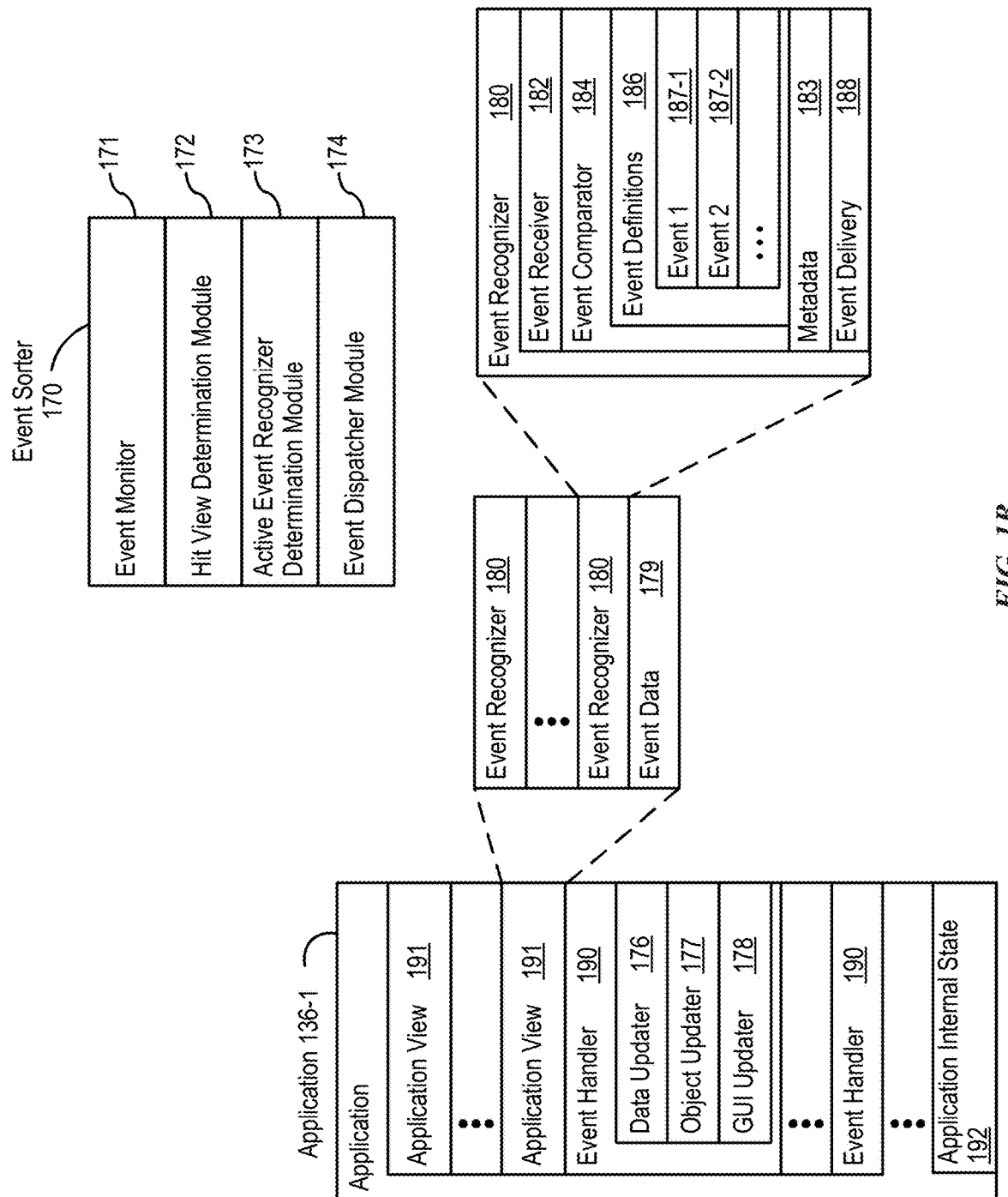
FIG. 1B is a block diagram illustrating exemplary components for event handling in accordance with some examples.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390)

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views, when touch sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;

Tray 408 with icons for frequently used applications, such as:

- Icon 416 for telephone module 138, labeled "Phone," which optionally includes an indicator 414 of the number of missed calls or voicemail messages;
- Icon 418 for e-mail client module 140, labeled "Mail," which optionally includes an indicator 410 of the number of unread e-mails;
- Icon 420 for browser module 147, labeled "Browser;" and
- Icon 422 for video and music player module 152, also referred to as iPod (trademark of Apple Inc.) module 152, labeled "iPod;" and Icons for other applications, such as:

- Icon 424 for IM module 141, labeled "Messages;"
- Icon 426 for calendar module 148, labeled "Calendar;"
- Icon 428 for image management module 144, labeled "Photos;"
- Icon 430 for camera module 143, labeled "Camera;"
- Icon 432 for online video module 155, labeled "Online Video"
- Icon 434 for stocks widget 149-2, labeled "Stocks;"
- Icon 436 for map module 154, labeled "Maps;"
- Icon 438 for weather widget 149-1, labeled "Weather;"
- Icon 440 for alarm clock widget 149-4, labeled "Clock;"
- Icon 442 for workout support module 142, labeled "Workout Support;"
- Icon 444 for notes module 153, labeled "Notes;" and
- Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 are labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch sensitive surface and the display are combined), in some embodiments, the device detects inputs on a touch-sensitive surface that is separate from the display, as shown in FIG. 4B. In some embodiments the touch sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
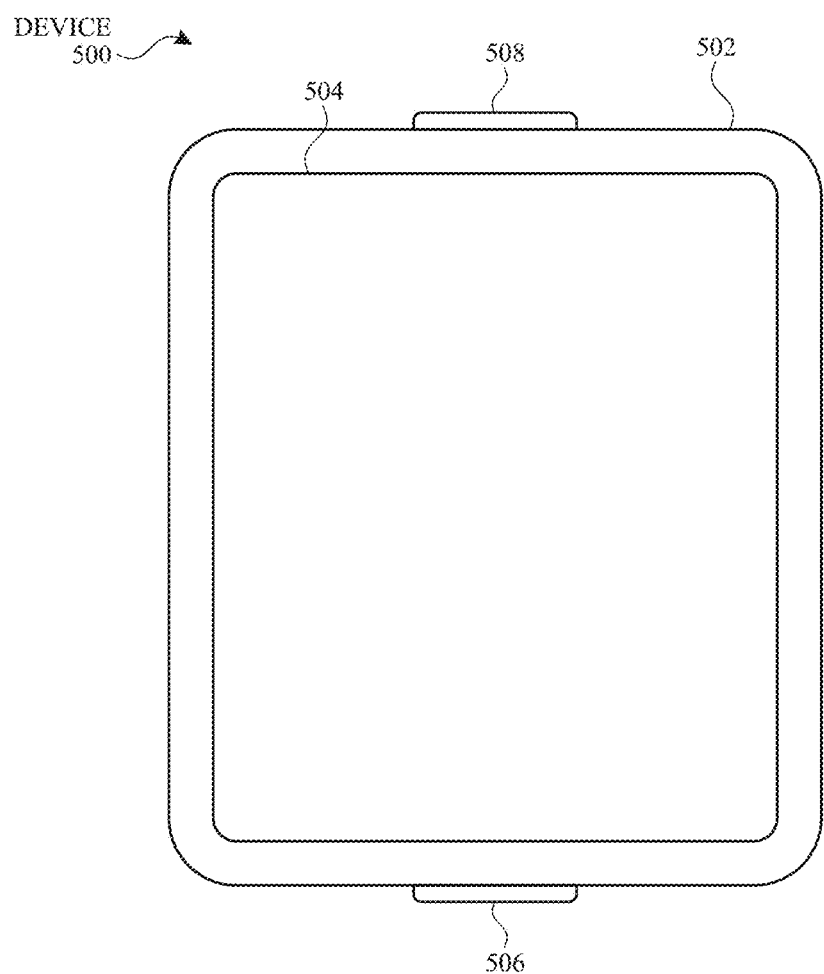
FIG. 5A illustrates a personal electronic device in accordance with some examples.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500. As used here, the term "intensity" of a contact (or touch) on touchscreen 504 (or the touch-sensitive surface) refers to the force or pressure (force per unit area) of a touch (e.g., a finger) on the touchscreen.

Personal electronic device 500 can be used for detecting and monitoring various attributes of a user's physical activity, such as an amount, an intensity level, a duration, a progress relative to a set value, a trend over a time period, or the like, of the activity, and can generate user interfaces for displaying the same. Device 500 can further be used to monitor a user's inactivity, where the user can be categorized as being inactive when device 500 detects that the user is not engaged in a physical activity that meets a predetermined criteria. For example, inactivity can be characterized by the absence of the user engaging in a physical activity that meets a threshold intensity (e.g., movement that expends a threshold number of Calories per unit time, movement that exceeds a threshold distance per unit time, or the like), the absence of the user engaging in a specified type of activity (e.g., standing, walking, running, swimming, climbing stairs, or the like), or a combination thereof. As will be described in greater detail below, device 500 can include various activity sensors for detecting activity and inactivity of a user and can generate an interface on a display of the device to provide the user with information associated with their activity or inactivity.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms may permit device 500 to be worn by a user.

In some examples, device 500 can further include an attachment mechanism (not shown) coupled to body 502 to permit device 500 to be worn by a user. The attachment mechanism can include a strap that permits device 500 to be worn around the user's wrist. However, it should be appreciated that the attachment mechanism can include other types of attachment mechanisms. For instance, in some examples, the attachment mechanism can include a string, a clip, a clasp, a metal loop, a toggle, a button, a snap, a hook, an interlocking part, a soldered part, or the like, that can be attached to or integrated with hats, eyewear, earrings, necklaces, shirts, jackets, bracelets, watch straps, chains, trousers, belts, shoes, purses, backpacks, hairbands, armbands, any other clothing, jewelry, or wearable accessories. In yet other examples, the attachment mechanism can include an adhesive, a weld metal, a polymer, a glue, or the like, that permits device 500 to be directly affixed to a user's body part, such as wrist, finger, toe, neck, head, arm, leg, ankle, waist, or the like.

Device 500 can further include one or more activity sensors for detecting physical activity of a user. The activity sensors can include one or more of global positioning system (GPS) sensors, pedometers, accelerometers, biometric sensors, gyroscope sensors, motion sensors, timer sensors, clock sensors, or the like, and can be operable to output activity data that represents various attributes of a detected activity of the user.

Figure 5B:
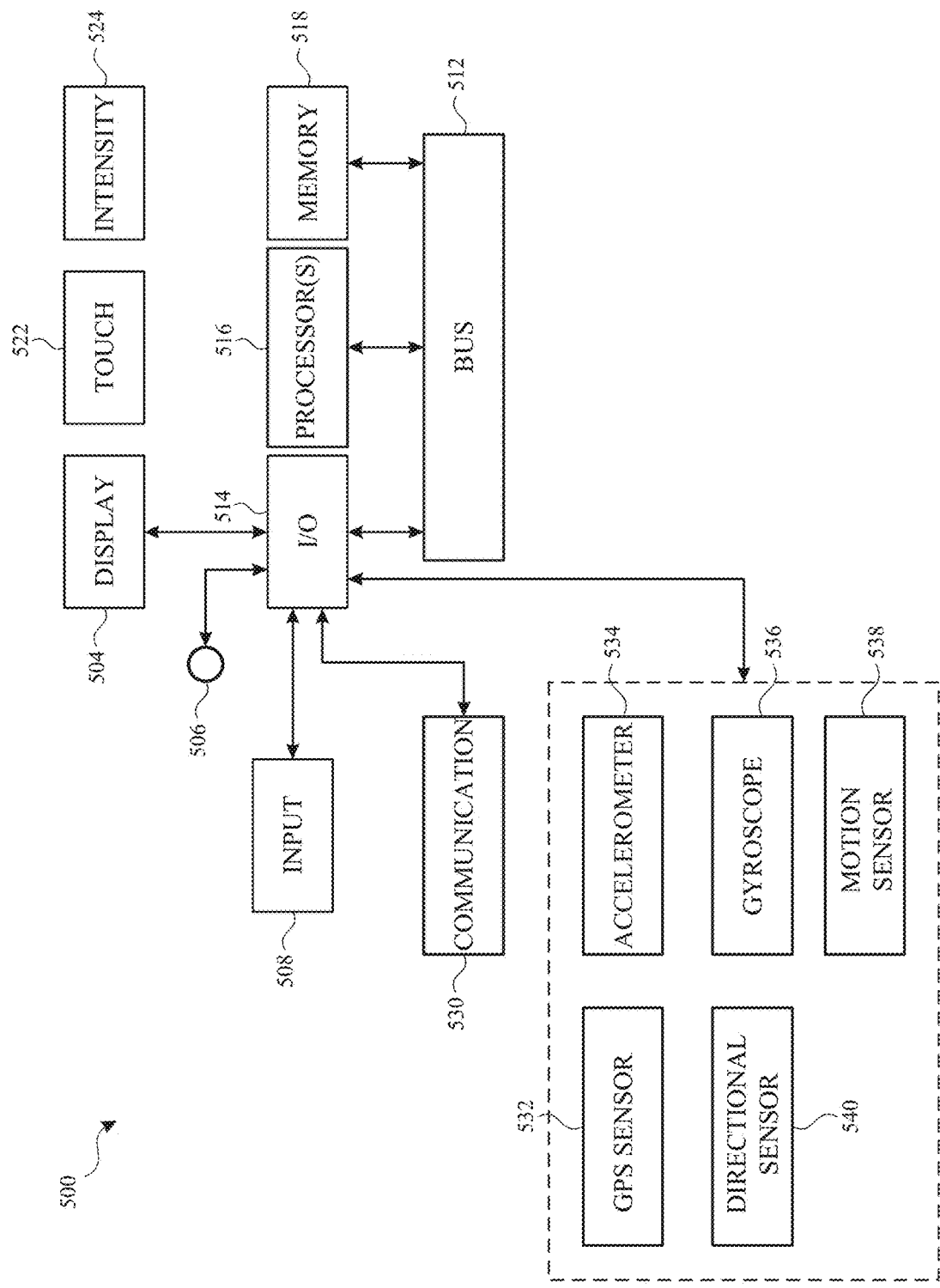
FIG. 5B is a block diagram illustrating a personal electronic device in accordance with some examples.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 531 for receiving application and operating system data, using Wi-Fi, Bluetooth™, near field communication (NFC), cellular and/or other wireless communication techniques. In some examples, communication unit 531 can be used to detect non-identical device types, such as smart phones or tablets of the same brand, that are running the same or compatible operating system as device 500. Communication unit 531 can also be used to identify different brands and/or types of devices that support communication over a common protocol. These protocols can include wireless protocols, such as Wi-Fi, Bluetooth™, NFC, or the like, as well as various software-based service protocols. Using one or more of these features, device 500 can sync with other devices and share information about the user's activity in real-time. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514. While not shown, other sensor(s) 541 can include any of a pedometer, a passive infrared sensor, an ultrasonic sensor, a microwave sensor, a tomographic motion detector, a camera, a biometric sensor, a light sensor, a timer, or the like.

In some examples, the biometric sensor can include one or more health-related optical sensors, capacitive sensors, thermal sensors, electric field (eField) sensors, and/or ultrasound sensors, such as photoplethysmogram (PPG) sensors, electrocardiography (ECG) sensors, and/or galvanic skin response (GSR) sensors. These sensors can generate data providing health-related information associated with the user. For example, PPG sensors can provide information regarding a user's respiratory rate, blood pressure, and/or oxygen saturation. ECG sensors can provide information regarding a user's heartbeats. GSR sensors can provide information regarding a user's skin moisture indicative of sweating and can prioritize a thermostat application to determine a user's body temperature. Using one or more of these sensors, device 500 can determine physiological characteristics of the user while performing a detected activity, such as a heart rate of a user associated with the detected activity, average body temperature of a user detected during the detected activity, any normal or abnormal physical conditions associated with the detected activity, or the like.

In some examples, GPS sensor 524 can be used to determine a user's location and movement, as well as a displacement of the user's motion. Accelerometer 526, directional sensor 528, and gyroscope 530 can further generate activity data that can be used to determine whether a user of device 500 is engaging in an activity, is inactive, or is performing a gesture. Device 500 can further include a timer that can be used, for example, to add time dimensions to various attributes of the detected physical activity, such as a duration of a user's physical activity or inactivity, time(s) of a day when the activity is detected or not detected, etc.

Activity sensors 520 can be embedded in body 502 of device 500, placed near a bottom surface of body 502 of device 500, or can be positioned at any other desirable location. In some examples, different activity sensors 520 can be placed in different locations inside or on the surfaces of device 500—e.g., some located inside body 502 and some attached to the attachment mechanism, or the like. In other examples, activity sensors 520 can be worn by a user separately from device 500. In such cases, the sensors can be configured to communicate with device 500 using a wired or wireless technology (e.g., via communication unit 531). In some examples, activity sensors 520 can be configured to communicate with each other and/or share data collected from one or more sensors. In some other examples, device 500 can be waterproof such that the sensors can detect a user's activity in water.

Figure 7:
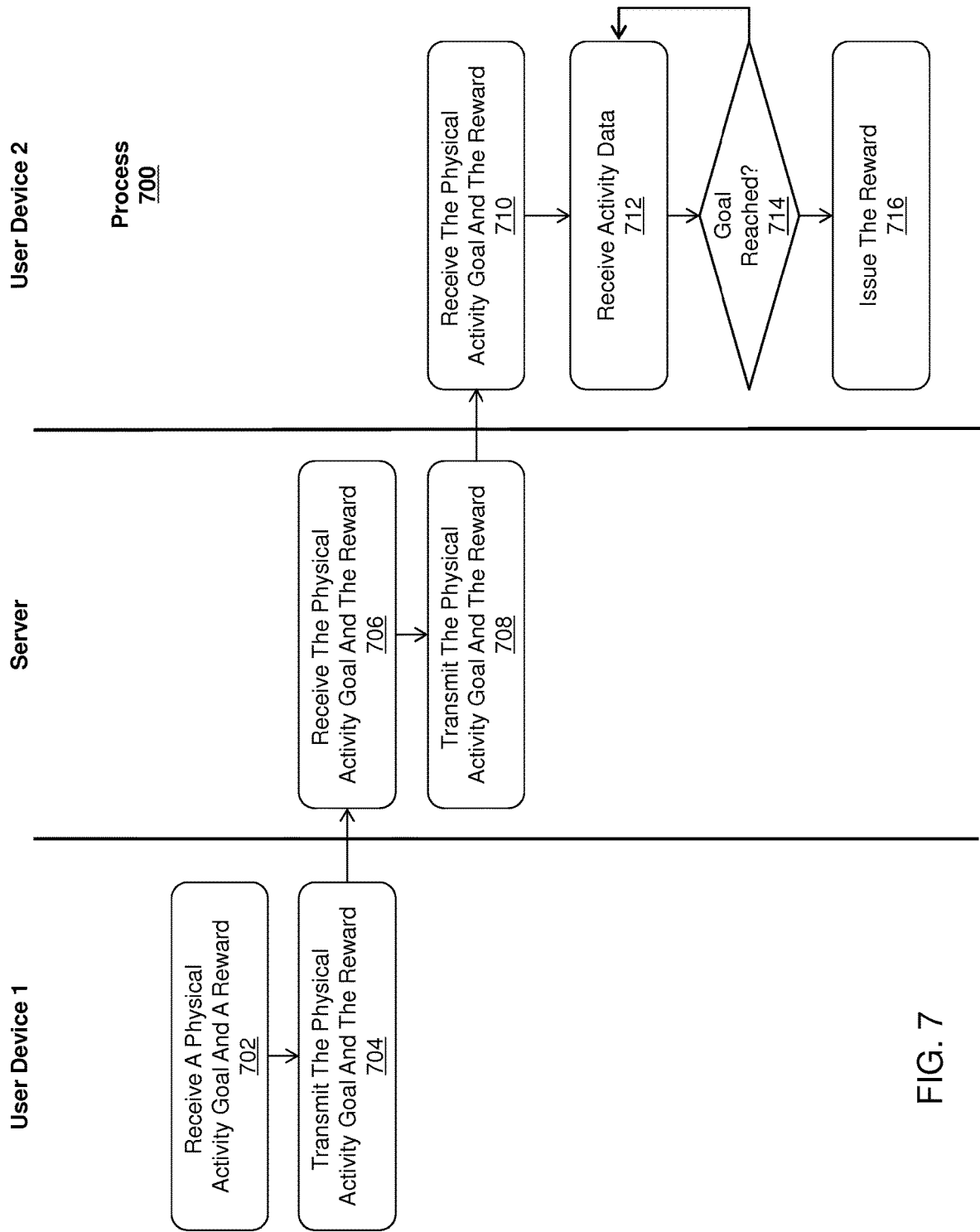
FIG. 7 illustrates processes for providing rewards to users for physical activity tracked using an electronic device according to various examples.
Figure 8:
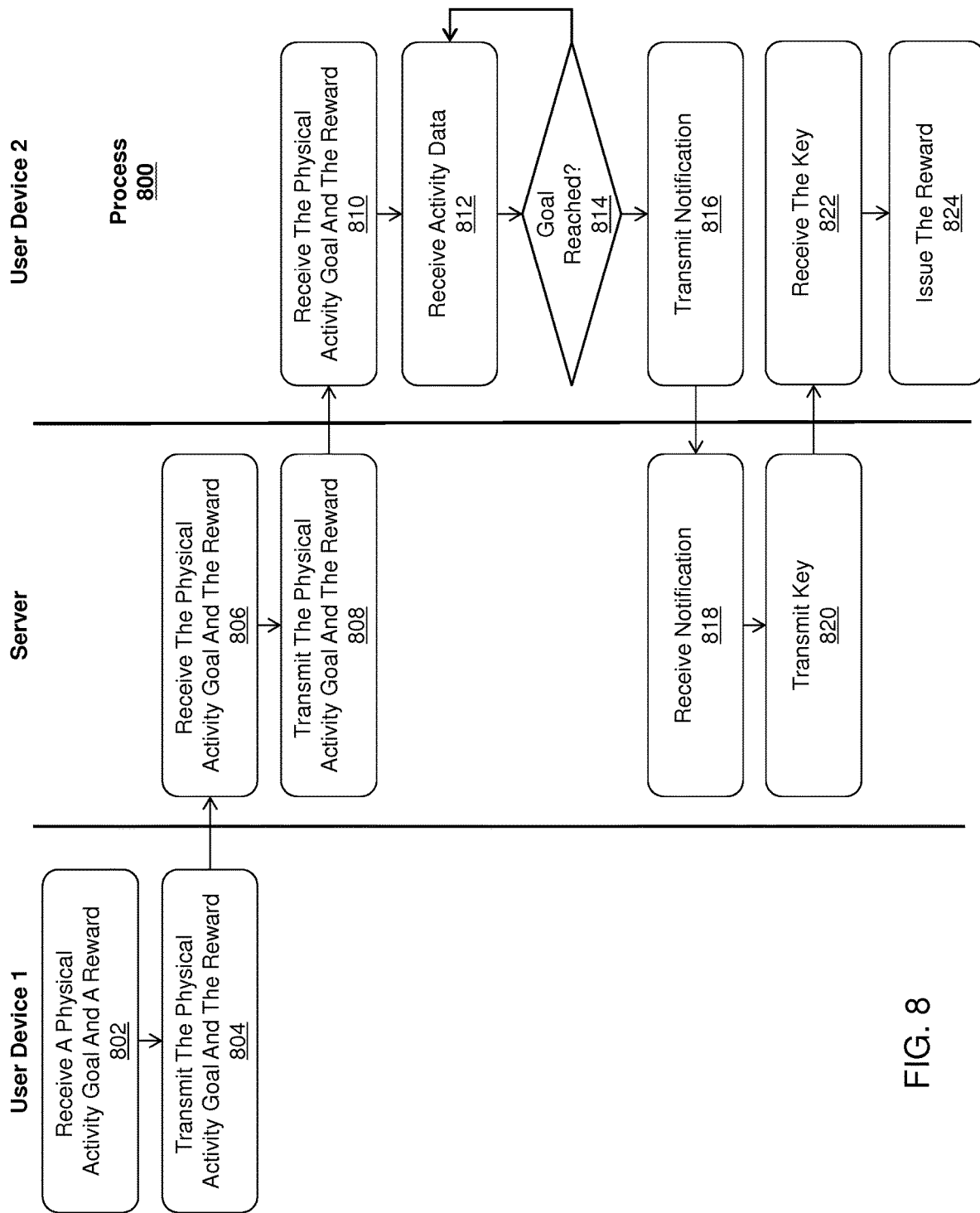
FIG. 8 illustrates processes for providing rewards to users for physical activity tracked using an electronic device according to various examples.
Figure 9:
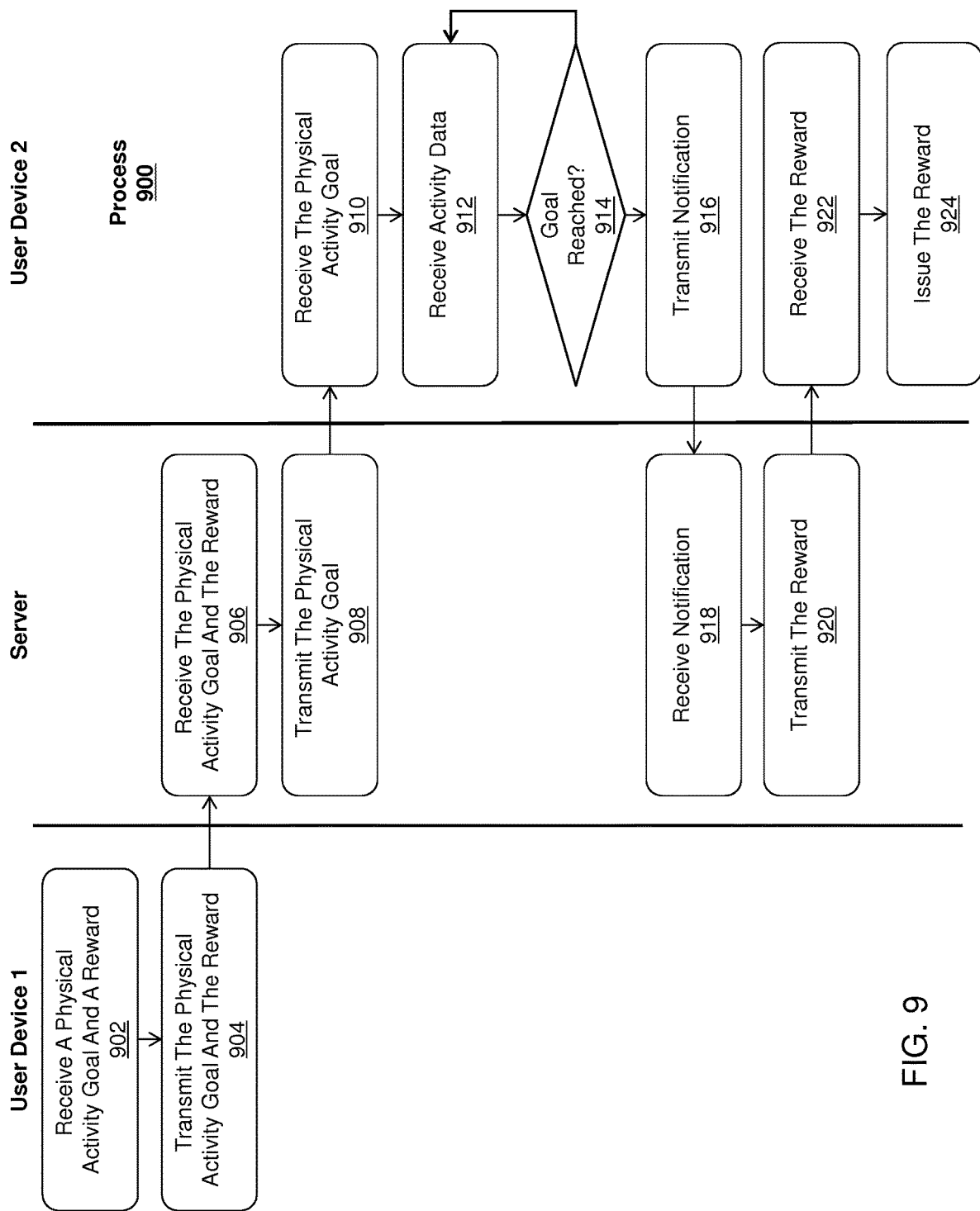
FIG. 9 illustrates processes for providing rewards to users for physical activity tracked using an electronic device according to various examples.

Memory 518 of computing device 500 can be a non-transitory computer readable storage medium, for storing computer-executable instructions, which, when executed by one or more computer processors 516, for example, can cause the computer processors to perform the techniques described above, including processes 700, 800, and 900 (FIGS. 7, 8, and 9). The computer-executable instructions can also be stored and/or transported within any non-transitory computer readable storage medium for use by or in connection with an instruction execution system, apparatus, or device, such as a computer-based system, processor-containing system, or other system that can fetch the instructions from the instruction execution system, apparatus, or device and execute the instructions. For purposes of this document, a "non-transitory computer readable storage medium" can be any medium that can tangibly contain or store computer-executable instructions for use by or in connection with the instruction execution system, apparatus, or device. The non-transitory computer readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Computing device 500 is not limited to the components and configuration of FIG. 5B, but can include other or additional components in multiple configurations.

Device 500 can further include one or more computer processors 516 coupled to memory section 518 via bus 512. I/O section 514 can be coupled to bus 512 to allow processors 516 and memory 518 to transmit and receive data from other components of device 500. For example, processors 516 can be coupled to provide instructions to activity sensors 520 via I/O section 514 and can be coupled to receive activity data from activity sensors 520 via I/O section 514.

Processors 516 can be configured to process the activity data to determine if the physical activity data represents a physical activity or a gesture being performed by the user, where a physical activity can generally refer to any bodily motion that can enhance or maintain physical fitness and overall health and wellness. Additionally, processors 516 can be configured to identify the type of physical activity represented by the activity data, such as whether the detected activity is standing, bicycling, jogging, walking, running, swimming, jumping, going up stairs, intense bodily movements, such as wrestling, or the like. Examples of gestures recognizable by device 500 include, but are not limited to, waving hands, moving fingers, such as typing, or the like. In some examples, processor 516 can determine a physical activity of a user based on one or more physical activity recognition algorithms. Some algorithms can instruct processor 516 to recognize movement of device 500 as being associated with a gesture if the detected movement does not have an intensity level greater than or equal to a physical activity threshold. The physical activity threshold can be represented as a distance traveled, a number of Calories burned, a number of steps taken, any one or more of these attributes calculated per unit time, or the like. The algorithms for storing such instructions for the one or more processors 516 can be stored in memory section 518.

Additionally, processors 516 can determine, based on the physical activity data received from the sensors, various attributes of the detected physical activity. Attributes of the detected physical activity can include physical, biological, physiological, or environmental characteristics associated with the detected physical activity. Examples of attributes determinable by device 500 upon detecting a physical activity can include, but are not limited to: duration of the detected physical activity; time(s) of a day when the user performs the detected physical activity; amount of Calories burned by a user of the device while performing the detected physical activity; distance travelled by a user of the device while performing the detected physical activity; steps taken by a user of the device while performing the detected physical activity; elevation climbed by a user of the device while performing the detected physical activity; highest/lowest/average velocity of a user of the device while performing the detected physical activity; highest/lowest/average heart rate of a user of the device while performing the detected physical activity; highest/lowest/average body temperature of a user of the device while performing the detected physical activity; or the like. For example, when device 500 categorizes a detected physical activity as walking, device 500 can further determine one or more attributes of the detected walking, such as a length of time for which the walking continues, highest/lowest/average speed of the user while walking, amount of Calories burned from the detected walking, or the like. In some examples, device 500 can further determine time dimensions associated with one or more attributes using a clock/timer sensor such as time(s) of a day when physical activity is detected, time(s) of a day when the most/least intensive physical activity is detected, time(s) of a day when a certain amount of Calories are burned, or the like.

In some examples, processors 516 in combination with activity sensors 520 of device 500 can detect when the system is placed into a viewing position. For instance, accelerometer 526, motion sensor 534, and/or gyroscope 530 can detect when device 500 is raised, lowered, and shaken. These sensors can also detect wrist rotation forward and backward. In some examples, the raising of device 500 can be interpreted as a placement of the device into viewing position. In other examples, the raising and rotation of device 500 can be interpreted as a placement of the device into viewing position. In yet other examples, the raising and rotation of device 500 within a threshold duration can be interpreted as a placement of the device into viewing position. When put into a viewing position, device 500 can adjust the display image according to the viewing positions and angles, and/or update the display image to reflect the most current data related to the user's physical activity. In some examples, device 500 can determine that when it is moving at a velocity that exceeds a threshold (e.g., 10 mph, 20 mph, 25 mph, 30 mph, 40 mph, 50 mph, 55 mph, 60 mph, 65 mph, etc.), the user of the device is commuting, and the movement associated with the user is not a result of the user's bodily movement or exercising. In other examples, device 500 can receive an input from a user indicating that he/she is engaging in a particular type of activity that causes them to move at a velocity exceeding the above-mentioned threshold (e.g., cycling), and that the associated movement should be interpreted as being a result of exercise.

In some other examples, device 500 can be globally turned off in response to a global turn-on/off signal. For instance, if globally turned off, device 500 can stop detecting and monitoring a physical activity from a user. This can advantageously save power in cases where the user intends to not use device 500 for a period of time. In some examples, a global turn-off signal can be inputted directly by a user of device 500 using an input mechanism of device 500. The user can set a period of time during which device 500 would be turned off and after which device 500 would automatically turn on. In other examples, a signal to turn off device 500 can be automatically generated in response to the processor determining, based on a contact temperature or other conditions detectable by the sensors, that device 100 is no longer being worn by a user.

Device 500 can track a user's physical activity over different lengths of time. For example, if device 500 monitors a user's daily activity, it can track one or more attributes of the user's physical activities performed on the same day and can store and reset the values of those attributes the next day. For instance, in some cases, device 500 can monitor a total amount of daily physical activity performed by the user, and this total amount can be updated in real time throughout the day for 24 hours as more activities are detected. After the 24 hours have passed, the total amount can be stored and reset. Device 500 can be configured to reset the attribute value at a specified time that is adjustable by a user. In other examples, device 500 can operate over different lengths of time, such as a half day, two days, a week, two weeks, a month, or the like, that can be adjustable by a user of device 500. Further, in some examples where device 500 monitors a user's physical activity over a relatively extended length of time, device 500 may not have enough memory capacity to track and store all of the attributes of the user's physical activities over such an extended length of time and can instead be configured to offload some or all of the data collected from the sensors on an external device (e.g., a remote server) that is remote from device 500. The external device can be configured to communicate with a plurality of devices 500, and store data collected from these devices. The external device can be further configured to execute computer instructions on the data and communicate the result with one or more of these devices 500.

As used here, the term "affordance" refers to a user-interactive graphical user interface object that is, optionally, displayed on the display screen of devices 100, 300, and/or 500 (FIGS. 1, 3, and 5). For example, an image (e.g., icon), a button, and text (e.g., hyperlink) each optionally constitute an affordance As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is optionally characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments the contact-detection intensity threshold is zero. In some embodiments the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

As used herein, an "installed application" refers to a software application that has been downloaded onto an electronic device (e.g., devices 100, 300, and/or 500) and is ready to be launched (e.g., become opened) on the device. In some embodiments, a downloaded application becomes an installed application by way of an installation program that extracts program portions from a downloaded package and integrates the extracted portions with the operating system of the computer system.

As used herein, the terms "open application" or "executing application" refer to a software application with retained state information (e.g., as part of device/global internal state 157 and/or application internal state 192). An open or executing application is, optionally, any one of the following types of applications:
- an active application, which is currently displayed on a display screen of the device that the application is being used on;
- a background application (or background processes) which is not currently displayed, but one or more processes for the application are being processed by one or more processors; and
- a suspended or hibernated application, which is not running, but has state information that is stored in memory (volatile and non-volatile, respectively) and that can be used to resume execution of the application.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

System Overview

Attention is now directed to systems and processes for providing rewards to users for physical activity tracked using an electronic device. In one example, a first user can challenge a second user to perform a physical activity goal. The first user can further provide a reward that is to be given to the second user in response to the second user completing the physical activity goal. An electronic device associated with the second user can be used to detect physical activity performed by the second user and to determine whether the second user has completed the physical activity goal. In response to determining that the second user has completed the physical activity goal, the reward can be issued to the second user. The reward can include an image, a video, a song, an electronic message (e.g., audio and/or text), an amount of virtual currency, access to a service, or the like.

Figure 6:
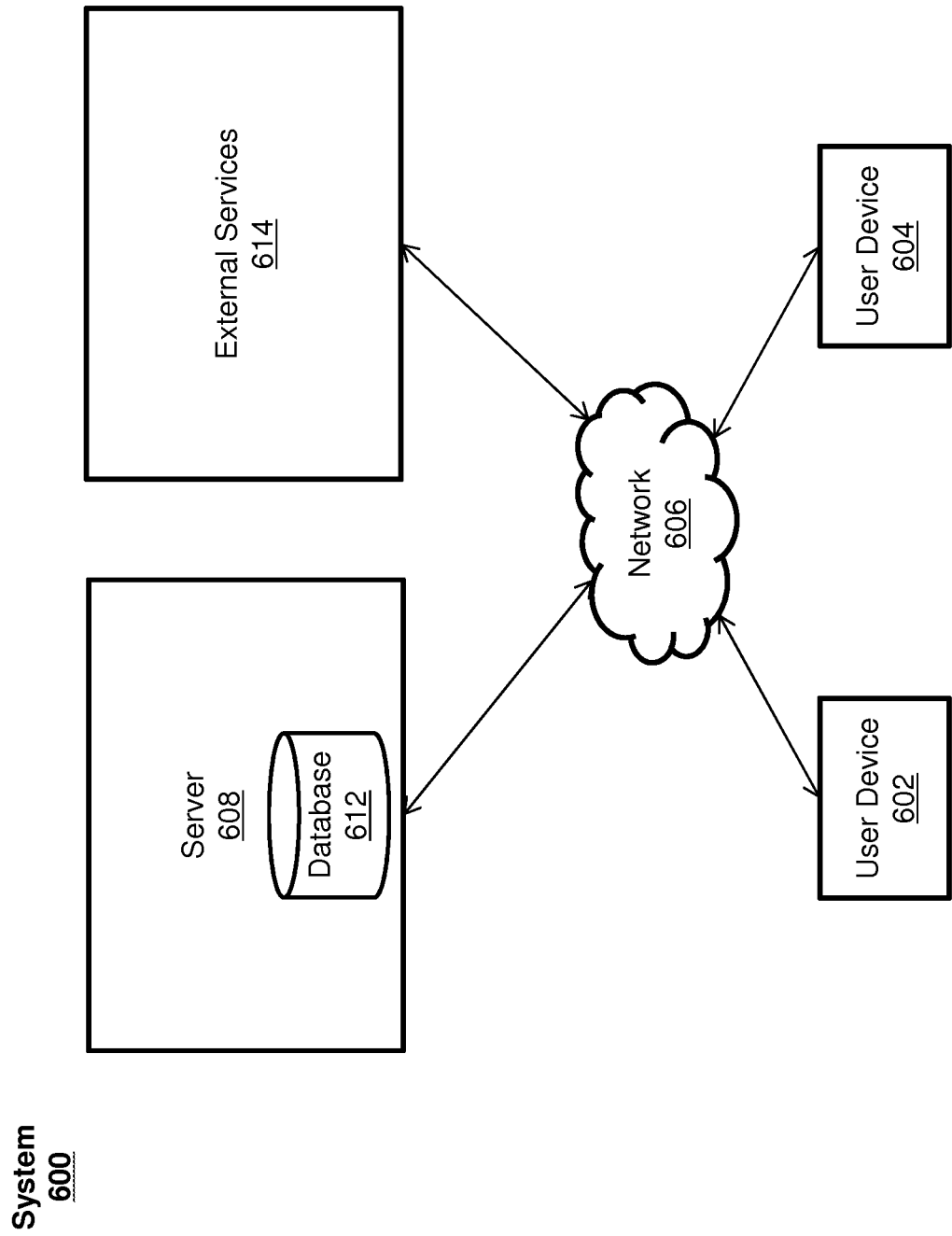
FIG. 6 illustrates a system for providing rewards to users for physical activity tracked using an electronic device according to various examples.

FIG. 6 illustrates an example system 600 for providing rewards to users for physical activity tracked using an electronic device according to various examples. System 600 can include a first user device 602 that is associated with a first user and that can include any type of electronic device, such as a mobile phone, tablet computer, desktop computer, laptop computer, PDA, wearable electronic device, or the like. System 600 can further include a second user device 604 associated with a second user. The second user device 604 can include any type of electronic device that is capable of detecting attributes of the second user's physical activity, such as a distance traveled, a location, a number of calories burned, a number of steps taken, or the like. In some examples, first user device 602 and/or second user device 604 can include a device similar or identical to device 100, 300, or 500. While not shown, system 600 can further include any number of additional user devices associated with any number of additional users. These additional user devices may or may not be capable of detecting attributes of the associated users' physical activity.

System 600 can further include server 608 coupled to user devices 602 and 604 via network 606, which can include the Internet, an intranet, or any other wired or wireless public or private network. As discussed in greater detail below with respect to FIGS. 7-9, server 608 can be configured to receive a physical activity goal from the user of user device 602 that is to be completed by the user of user device 604, receive a reward from the user of user device 602 that is to be given to the user of user device 604 in response to the user of user device 604 completing the physical activity goal, and issuing the reward to the user of user device 604 in response to the user of user device 604 completing the physical activity goal. The physical activity goal can include an amount of physical activity to be performed, a location to be reached, a frequency of engaging in physical activity, meeting a condition within a time constraint, or the like. The reward can include any type of reward, such as a media file (e.g., an image file, a video file, a music file, an electronic text document), an electronic message, an amount of virtual currency, a key or passcode for unlocking a service (e.g., use of a television, video game, etc.), or the like. In some examples, the reward can be received from user device 602 by server 608 and can be stored in a local or remote database 612. In other examples, the reward can already exist in database 612. In yet other examples, the reward can be provided by an external service 614, such as an electronic media provider. In these examples, server 608 can communicate with the server(s) of external services 614 to provide the reward to the user of user device 604 in response to the user of user device 604 completing the physical activity goal. In this way, the user of device 602 can challenge the user of device 604 to a physical activity goal, and thereby encourage the user of device 604 to perform physical activities.

FIG. 7 illustrates an exemplary process 700 for providing rewards to users for physical activity tracked using an electronic device according to various examples. In some examples, process 700 can be performed using a system similar or identical to system 600. In these examples, the blocks in the left column of FIG. 7 can represent operations performed by a first user device (e.g., user device 602), the blocks in the middle column of FIG. 7 can represent operations performed by one or more servers (e.g., server 608), and the blocks in the right column of FIG. 7 can represent operations performed by a second user device (e.g., user device 604). In some examples, the second user device can include a device similar or identical to device 500 for detecting and monitoring the physical activity performed by the second user.

At block 702, a first user device (e.g., user device 602) associated with a first user can receive an identification of a second user (e.g., user of user device 604), a physical activity goal to be performed by the second user, and a reward that is to be given to the second user in response to the second user achieving the physical activity goal.

In some examples, the identification of the second user received at block 702 can include a name, a username, an account number, device identification number, or any other identifier that can be used to uniquely identify the second user. The identification can be received by the first user device using any desired input mechanism, such as a selection of the second user from a list of users (e.g., a contact list, a predefined group, etc.), entry of the second user's name or contact information in a text entry field, or the like.

In some examples, the physical activity goal received at block 702 can include one or more of an amount of physical activity to be performed, a location to be reached, a frequency of engaging in physical activity, meeting a condition within a time constraint, or the like. For example, one physical activity goal can require that the second user burn 200 calories (amount of physical activity to be performed) within the next 3 hours (time constraint). Another physical activity goal can require that the second user go to the gym (location to be reached) on a specified day (time constraint). Yet another physical activity goal can require that the second user run at least 3 miles (an amount of physical activity to be performed) for 5 consecutive days within the next week (frequency of engaging in physical activity and a time constraint). The physical activity goal can be received by the first user device using any desired input mechanism, such as a selection of the goal from a list of predetermined goals, entry of the goal using a text entry field, selection of a location from a map, or the like.

In some examples, receiving the reward at block 702 can include receiving an identification of the reward or the reward itself. For example, receiving the reward can include receiving an identification of a music file available for purchase from an online media provider, or can include receiving the music file itself. The types of rewards that can be received can include a media file (e.g., an image file, a video file, a music file, an electronic text document), an electronic message, an amount of virtual currency, a key or passcode for unlocking a service (e.g., use of a television, video game, etc.), or the like. In some examples, the reward can be generated by the first user device. For example, the first user device can be used to generate the reward by capturing an image, recording a video, or generating an electronic message that is to be used as the reward. This can be done, for example, to allow a son or daughter to send an image or video as a reward to motivate their father to engage in physical activity. In other examples, the reward can include a media file (e.g., an image file, a video file, a music file, or an electronic text document), an electronic message, an amount of virtual currency, a key or passcode for unlocking a service (e.g., use of a television, video game, etc.) located at a remote device, such as a remote server (e.g., server 608 or 614). In some examples, the remotely located reward can be associated with a fee. For example, the reward can include a music file available for purchase or rent from an online media service. In these examples, upon successful completion of the physical activity goal, the reward can be given to the second user with the associated fee being charged to the first user.

In some examples, an identification of more than one user can be received at block 702. In these examples, the physical activity goal received at block 702 can be a goal that is to be performed by all of the identified users. Depending on the physical activity goal, the reward can be given to all users that successfully complete the physical activity goal, the first user that completes the physical activity goal, or any other desired subset of users that complete the physical activity goal.

At block 704, the first user device can transmit the identification of the second user, the physical activity goal, and the reward to one or more servers. For example, the first user device 602 can transmit the information to server 608 via network 606. In examples where the first user device generates the reward, the generated reward (e.g., image file, video file, electronic message, etc.) can be transmitted to the server at block 404. In other examples where the reward is located at a remote location, an identification (e.g., file name, file location, etc.) of the reward can be transmitted to the server at block 704.

At block 706, the one or more servers can receive the identification of the second user, the physical activity goal, and the reward from the first user device. For example, server 608 can receive the identification of the second user, the physical activity goal, and the reward from user device 602 via network 606.

At block 708, the one or more servers can transmit the physical activity goal and the reward to the second user (using the received identification of the second user). For example, server 608 can transmit the physical activity goal and the reward to user device 604 via network 606. In examples where the reward itself was received from the first user device or where the reward was previously located at the one or more servers, the one or more servers can transmit the reward in an encrypted or non-encrypted form. In other examples where the reward was located at another remote device (e.g., server 614), block 708 can include transmitting a message to the other remote device to cause the other remote device to transmit the reward to the second user device in an encrypted or non-encrypted form.

At block 710, the second user device can receive the physical activity goal and the reward from the one or more servers. For example, user device 604 can receive the physical activity goal and the reward from server 608 via network 606. In some examples, the second user device can store the reward on a storage device within the second user device in an unreleased state. The unreleased state can represent a state in which access to the reward is restricted. For example, the second user device can store the reward in such a way that prevents a user from viewing an image file reward, playing a video file reward, listening to a music file reward, viewing an electronic text document reward, viewing an electronic message reward, accessing a key or passcode for unlocking a service (e.g., television, video game, etc.), or the like.

At block 712, one or more processors of the second user device can receive activity data that is representative of sensed physical activity of a user from one or more activity sensors (e.g., sensors similar or identical to sensors 520) of the second user device. The one or more processors can process the received activity data to update a value of one or more attributes of the user's physical activity. For example, activity data from a timer can be used to update a duration of the user's physical activity. Additionally, activity data from accelerometer 526, motion sensor 534, gyroscope 530, biometric sensor, and/or GPS sensor 524 can be used to update a distance traveled and can additionally or alternatively be used to update a number of calories burned (in combination with the user's age, gender, and weight). It should be appreciated that activity data from other activity sensors 520 can similarly be used to determine and update values of other attributes of the user's physical activity.

At block 714, the one or more processors can determine whether the physical activity goal received at block 710 has been reached based on the physical activity data received at block 712. If it is determined that the physical activity goal has not been reached, the process can return to block 712. Blocks 714 and 712 can repeatedly be performed to update the one or more attributes of the user's physical activity until either the physical activity goal is reached or the physical activity goal expires (e.g., based on a time constraint of the physical activity goal expiring). If it is instead determined at block 714 that the physical activity goal has been reached, the process can proceed to block 716.

For example, if the physical activity goal includes an amount of physical activity to be performed, it can be determined whether an aggregate amount of physical activity is greater than or equal to the physical activity goal. The aggregate amount of physical activity can include physical activity sensed during the period of time that is relevant to the physical activity goal. For example, if the physical activity goal included a constraint that the goal must be achieved within a threshold length of time, the aggregate amount of physical activity can include sensed physical activity between the time the physical activity goal was received at block 702 or 710 and the expiration of the threshold length of time. If it is determined that the aggregate amount of physical activity is not greater than or equal to the physical activity goal, the process can return to block 712. If it is instead determined at block 714 that the aggregate amount of physical activity is greater than or equal to the physical activity goal, the process can proceed to block 716.

In other examples, if the physical activity goal includes a location to be reached, it can be determined (e.g., using GPS sensor 524) whether a location of the user is within a threshold distance from the goal location. If it is determined that the location of the user is not within the threshold distance from the goal location, the process can return to block 712. If it is instead determined at block 714 that the user is within the threshold distance from the goal location, the process can proceed to block 716.

At block 716, the reward can be issued to the user. For example, user device 604 can issue the reward to the second user. In some examples, issuing the reward can include changing the state of the previously inaccessible reward stored at block 710 to a released state in which access to the reward is allowed. For example, the second user device can allow the second user to view an image file reward, play a video file reward, listen to a music file reward, view an electronic text document reward, view an electronic message reward, access a key or passcode for unlocking a service (e.g., television, video game, etc.), or the like.

In some examples, a notification that the reward has been issued can be transmitted from the second user device to the one or more server. The one or more servers can then notify the first user device that the reward has been issued. For example, the second user device 604 can transmit a notification that the reward has been issued to server 608, which can then transmit the notification to first user device 602.

Using process 700, a first user can create a physical activity goal and a reward for a second user to advantageously motivate the second user to engage in physical activity. Additionally, process 700 can be used to create physical activity related games, such as a scavenger hunt or chain letter type game. For example, a first user can create a physical activity goal for one or more users. The reward given in response to completion of the physical activity goal can include a first location of the scavenger hunt. Upon obtaining the first location of the scavenger hunt, additional physical activity goals and rewards can be provided for each remaining location of the scavenger hunt. In another example, a first user can create a physical activity goal for a second user. The reward given in response to completion of the physical activity goal can include a name of a third user. The second user can then create a physical activity goal for the third user and a reward containing the name of a fourth user. The process can continue on for a threshold length of time or until a random or predetermined time. The user currently in possession of the physical activity goal and the unlocked reward can be considered the loser of the game.

While the example described above for process 700 include interaction between two users, it should be appreciated that the physical activity goal and reward received at block 702 can be selected for any number of other users. In these examples, the physical activity goal received at block 702 can be a goal that is to be performed by all of the identified users. In some examples, the users can be notified that other users are also receiving the physical activity goal while, in other examples, the users may not be notified that other users are also receiving the physical activity goal. Depending on the physical activity goal, the reward can be issued to all users that successfully complete the physical activity goal, the first user that completes the physical activity goal, or any other desired subset of users that complete the physical activity goal. Restriction of the issuance of the rewards can be achieved by an additional update messages transmitted between the one or more servers and the one or more recipient users. The update messages can notify the one or more servers when the first user completes the physical activity goal and/or notify the one or more user devices when the reward can no longer be obtained.

FIG. 8 illustrates another exemplary process 800 for providing rewards to users for physical activity tracked using an electronic device according to various examples. Process 800 can be similar to process 700, except that access to the reward can be granted by the one or more servers in response to the second user device determining that the physical activity goal has been reached. In some examples, process 800 can be performed using a system similar or identical to system 600. In these examples, the blocks in the left column of FIG. 8 can represent operations performed by a first user device (e.g., user device 602), the blocks in the middle column of FIG. 8 can represent operations performed by one or more servers (e.g., server 608), and the blocks in the right column of FIG. 8 can represent operations performed by a second user device (e.g., user device 604). In some examples, the second user device can include a device similar or identical to device 500 for detecting and monitoring the physical activity performed by the second user.

Blocks 802, 804, 806, 808, 810, 812, and 814 can be similar to blocks 702, 704, 706, 708, 710, 712, and 714, respectively. However, the reward transmitted at block 808 can be transmitted in encrypted form, preventing the second user device from being able to access its contents. At block 816, rather than issue the reward as is done at block 716 of process 700, the second user device can transmit a notification to the one or more servers that the second user has achieved the physical activity goal. For example, second user device 604 can transmit a notification to server 608 via network 606.

At block 818, the one or more servers can receive the notification from the second user device. For example, server 608 can receive the notification from user device 604 via network 606. At block 820, an encryption key or other information that can be used by the second user device to decrypt the reward (encrypted by the one or more servers at block 808) can be transmitted to the second user device. For example, server 608 can transmit the encryption key or other information that can be used to decrypt the reward to second user device 604 via network 606.

At block 822, the encryption key or other information that can be used to decrypt the reward can be received by the second user device. For example, second user device 604 can receive the encryption key or other information that can be used to decrypt the reward from server 608 via network 606. At block 822, the second user device can further decrypt the reward using the received encryption key or other information. At block 824, the second user device can issue the reward to the second user in a manner similar or identical to block 716 of process 700.

In some examples, a notification that the reward has been issued can be transmitted from the second user device to the one or more server. The one or more servers can then notify the first user device that the reward has been issued. For example, the second user device 604 can transmit a notification that the reward has been issued to server 608, which can then transmit the notification to first user device 602.

While the example described above for process 800 include interaction between two users, it should be appreciated that the physical activity goal and reward received at block 802 can be selected for any number of other users. In these examples, the physical activity goal received at block 802 can be a goal that is to be performed by all of the identified users. In some examples, the users can be notified that other users are also receiving the physical activity goal while, in other examples, the users may not be notified that other users are also receiving the physical activity goal. Depending on the physical activity goal, the reward can be issued to all users that successfully complete the physical activity goal, the first user that completes the physical activity goal, or any other desired subset of users that complete the physical activity goal. Restriction of the issuance of the rewards can be achieved by the one or more servers only transmitting the key or other information that can be used to decrypt the reward to the appropriate subset of user devices that complete the physical activity goal.

FIG. 9 illustrates another exemplary process 900 for providing rewards to users for physical activity tracked using an electronic device according to various examples. Process 900 can be similar to process 800, except that the reward may only be transmitted to the second user device in response to the second user device determining that the physical activity goal has been reached. In some examples, process 900 can be performed using a system similar or identical to system 600. In these examples, the blocks in the left column of FIG. 9 can represent operations performed by a first user device (e.g., user device 602), the blocks in the middle column of FIG. 9 can represent operations performed by one or more servers (e.g., server 608), and the blocks in the right column of FIG. 9 can represent operations performed by a second user device (e.g., user device 604). In some examples, the second user device can include a device similar or identical to device 500 for detecting and monitoring the physical activity performed by the second user.

Blocks 902, 904, and 906 can be similar to blocks 702/702, 704/804, and 706/806, respectively. However, at block 908, the one or more servers can store the reward and may only transmit the physical activity goal to the second user device. For example, server 608 can store the reward in database 612 and may transmit the physical activity goal (without transmitting the reward) to second user device 604 via network 606.

At block 910, the second user device can receive the physical activity goal from the one or more servers. For example, user device 604 can receive the physical activity goal from server 608 via network 606. Blocks 912 and 914 can be similar or identical to blocks 712/812 and 714/814, respectively. Blocks 916 and 918 can be similar or identical to blocks 816 and 818, respectively.

At block 920, the one or more servers can transmit the reward to the second user device. For example, server 608 can transmit the reward (e.g., an image file, a video file, a music file, an electronic text document, an electronic message, an amount of virtual currency, a key or passcode for unlocking a service, or the like) previously stored in database 612 to second user device 604 via network 606. In some examples, since it has already been determined that the second user has reached the physical activity goal, the reward may not be encrypted, thereby allowing the second user device to provide access to the reward upon receipt.

At block 922, the second user device can receive the reward from the one or more servers. For example, second user device 604 can receive the reward from server 608 via network 606. At block 924, the second user device can issue the reward to the second user in a manner similar or identical to blocks 716 and 824.

In some examples, a notification that the reward has been issued can be transmitted from the second user device to the one or more server. The one or more servers can then notify the first user device that the reward has been issued. For example, the second user device 604 can transmit a notification that the reward has been issued to server 608, which can then transmit the notification to first user device 602.

While the example described above for process 900 include interaction between two users, it should be appreciated that the physical activity goal and reward received at block 902 can be selected for any number of other users. In these examples, the physical activity goal received at block 902 can be a goal that is to be performed by all of the identified users. In some examples, the users can be notified that other users are also receiving the physical activity goal while, in other examples, the users may not be notified that other users are also receiving the physical activity goal. Depending on the physical activity goal, the reward can be issued to all users that successfully complete the physical activity goal, the first user that completes the physical activity goal, or any other desired subset of users that complete the physical activity goal. Restriction of the issuance of the rewards can be achieved by the one or more servers only transmitting the reward to the appropriate subset of user devices that complete the physical activity goal.

Electronic Device

Figure 10:
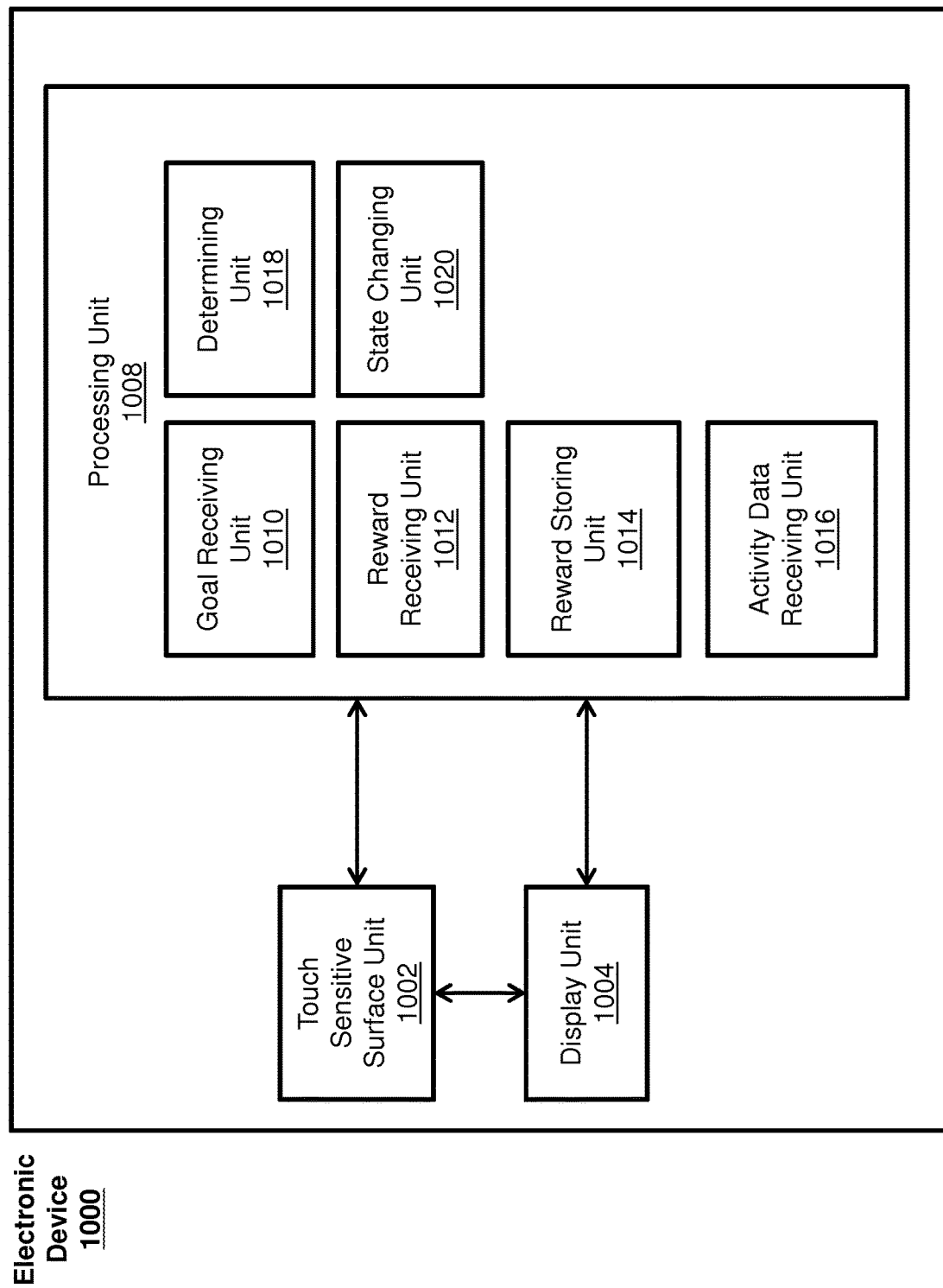
FIG. 10 illustrate functional block diagrams of electronic devices configured to provide rewards to users for physical activity tracked using an electronic device according to various examples.

In accordance with some examples, FIG. 10 shows a functional block diagram of an electronic device 1000 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 10 can be combined or separated into sub-blocks to implement the principles of the various described examples. Therefore, the description herein optionally supports any possible combination or separation or further definition of the functional blocks described herein.

As shown in FIG. 10, electronic device 1000 can include a display unit 1004 configured to display graphical objects, a touch-sensitive surface unit 1002 configured to receive user gestures, and a processing unit 1008. In some examples, processing unit 1008 can include goal receiving unit 1010, reward receiving unit 1012, reward storing unit 1014, activity data receiving unit 1016, determining unit 1018, and state changing unit 1020.

Processing unit 1008 can be configured to receive (e.g., using goal receiving unit 1010) a physical activity goal to be completed by a user associated with the electronic device. Reward receiving unit 1012 can be configured to receive a reward that is to be given to the user in response to the user completing the physical activity goal. Reward storing unit 1014 can be configured to store the reward in an unreleased state, wherein access to the reward is restricted while in the unreleased state. Activity data receiving unit 1016 can be configured to receive activity data generated by an activity sensor of the electronic device, wherein the activity data is representative of movement associated with the electronic device that is detected by the activity sensor. Determining unit 1018 can be configured to determine, based on the activity data, whether the user has completed the physical activity goal. State changing unit 1020 can be configured to change, in accordance with a determination that the user has completed the physical activity goal, the state of the reward to a released state, wherein access to the reward is allowed while in the released state.

In some examples, the physical activity goal includes an amount of physical activity to be performed by the user; and a duration during which the amount of physical activity is to be performed by the user. In some examples, determining, based on the activity data, whether the user has completed the physical activity goal includes: determining an aggregate amount of physical activity performed by the user based on the activity data; determining whether the aggregate amount of physical activity performed by the user is greater than or equal to the amount of physical activity to be performed by the user; and determining whether the duration during which the amount of physical activity is to be performed by the user has elapsed. In some examples, determining that the user has completed the physical activity goal includes: determining that the aggregate amount of the physical activity performed by the user is greater than or equal to the amount of physical activity to be performed by the user; and determining that the duration during which the amount of physical activity is to be performed by the user has not elapsed.

In some examples, the amount of physical activity to be performed by the user comprises a number of calories to expend, a distance to travel, or a number of steps to be taken.

In some examples, the physical activity goal includes: a location to be traveled to by the user; and a duration during which the location is to be traveled to by the user.

In some examples, determining, based on the activity data, whether the user has completed the physical activity goal includes: determining a location of the electronic device based on the activity data; determining whether the location of the electronic device is within a threshold distance from the location to be traveled to by the user; and determining whether the duration during which the location is to be traveled to by the user has elapsed. In some examples, determining that the user has completed the physical activity goal includes: determining that the location of the electronic device is within the threshold distance from the location to be traveled to by the user; and determining that the duration during which the location is to be traveled to by the user has not elapsed.

In some examples, the reward includes an image, a video, a song, an audio message, an electronic text document, or an amount of virtual currency. In some examples, device 1000 is a wearable electronic device.

Figure 11:
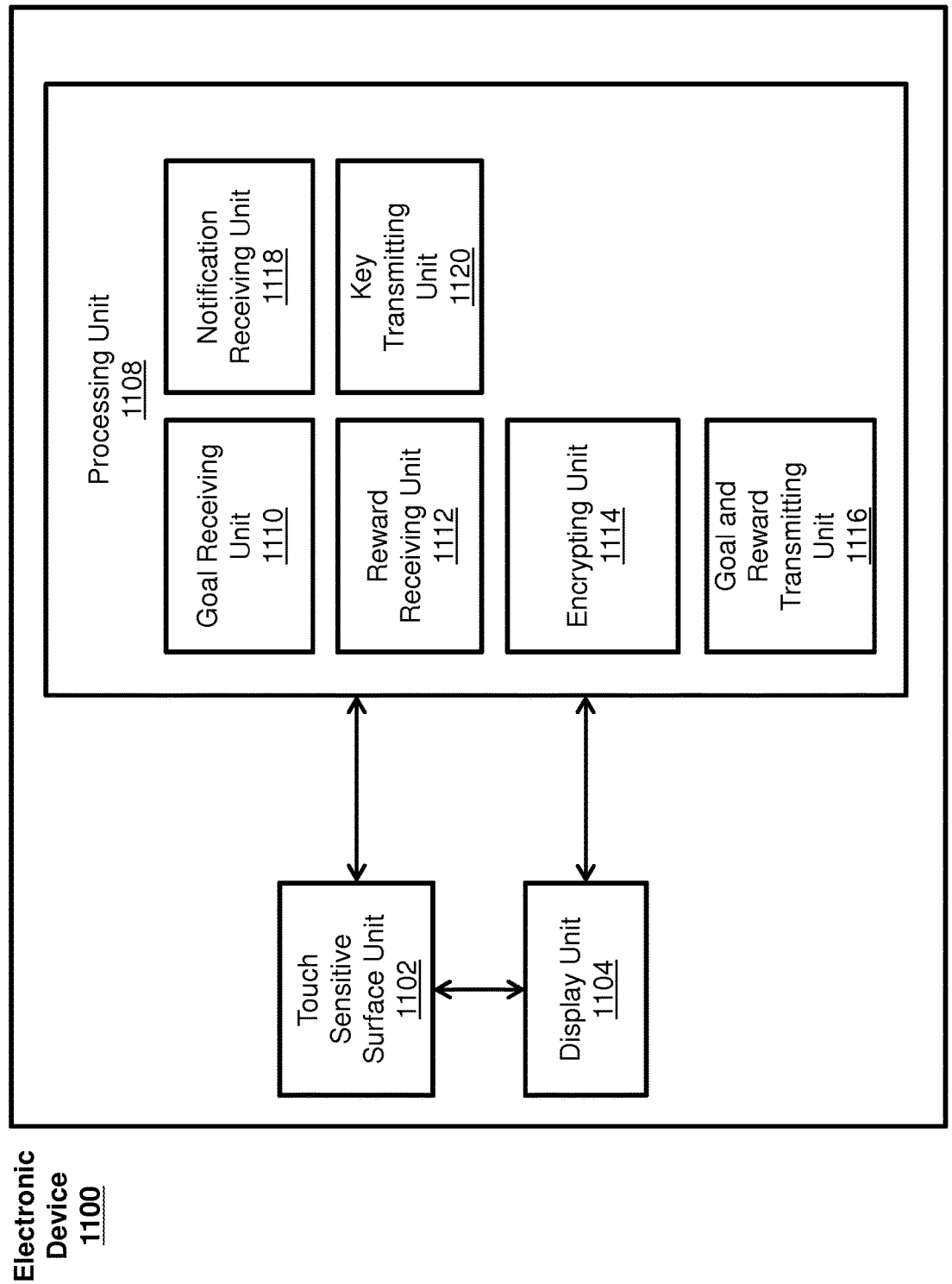
FIG. 11 illustrate functional block diagrams of electronic devices configured to provide rewards to users for physical activity tracked using an electronic device according to various examples.

In accordance with some examples, FIG. 11 shows a functional block diagram of an electronic device 1100 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 11 can be combined or separated into sub-blocks to implement the principles of the various described examples. Therefore, the description herein optionally supports any possible combination or separation or further definition of the functional blocks described herein.

As shown in FIG. 11, electronic device 1100 can include a display unit 1104 configured to display graphical objects, a touch-sensitive surface unit 1102 configured to receive user gestures, and a processing unit 1108. In some examples, processing unit 1108 can include goal receiving unit 1110, reward receiving unit 1112, encrypting unit 1114, goal and reward transmitting unit 1116, notification receiving unit 1118, and key transmitting unit 1120.

Processing unit 1108 can be configured to receive (e.g., using goal receiving unit 1110), from a first user device, a physical activity goal to be completed by a user associated with a second user device. Reward receiving unit 1112 can be configured to receive, from the first user device, a reward that is to be given to the user in response to the user completing the physical activity goal. Encrypting unit 1114 can be configured to encrypt the reward. Goal and reward transmitting unit 1116 can be configured to transmit the physical activity goal and the encrypted reward to the second user device. Notification receiving unit 1118 can be configured to receive, from the second user device, a notification that the user completed the physical activity goal. Key transmitting unit 1120 can be configured to transmit, in response to receiving the notification, a key for decrypting the encrypted reward to the second user device.

In some examples, the physical activity goal includes: an amount of physical activity to be performed by the user; and a duration during which the amount of physical activity is to be performed by the user. In some examples, the amount of physical activity to be performed by the user includes a number of calories to expend, a distance to travel, or a number of steps to be taken.

In some examples, the physical activity goal includes: a location to be traveled to by the user; and a duration during which the location is to be traveled to by the user.

In some examples, the reward includes an image, a video, a song, an audio message, an electronic text document, or an amount of virtual currency.

Figure 12:
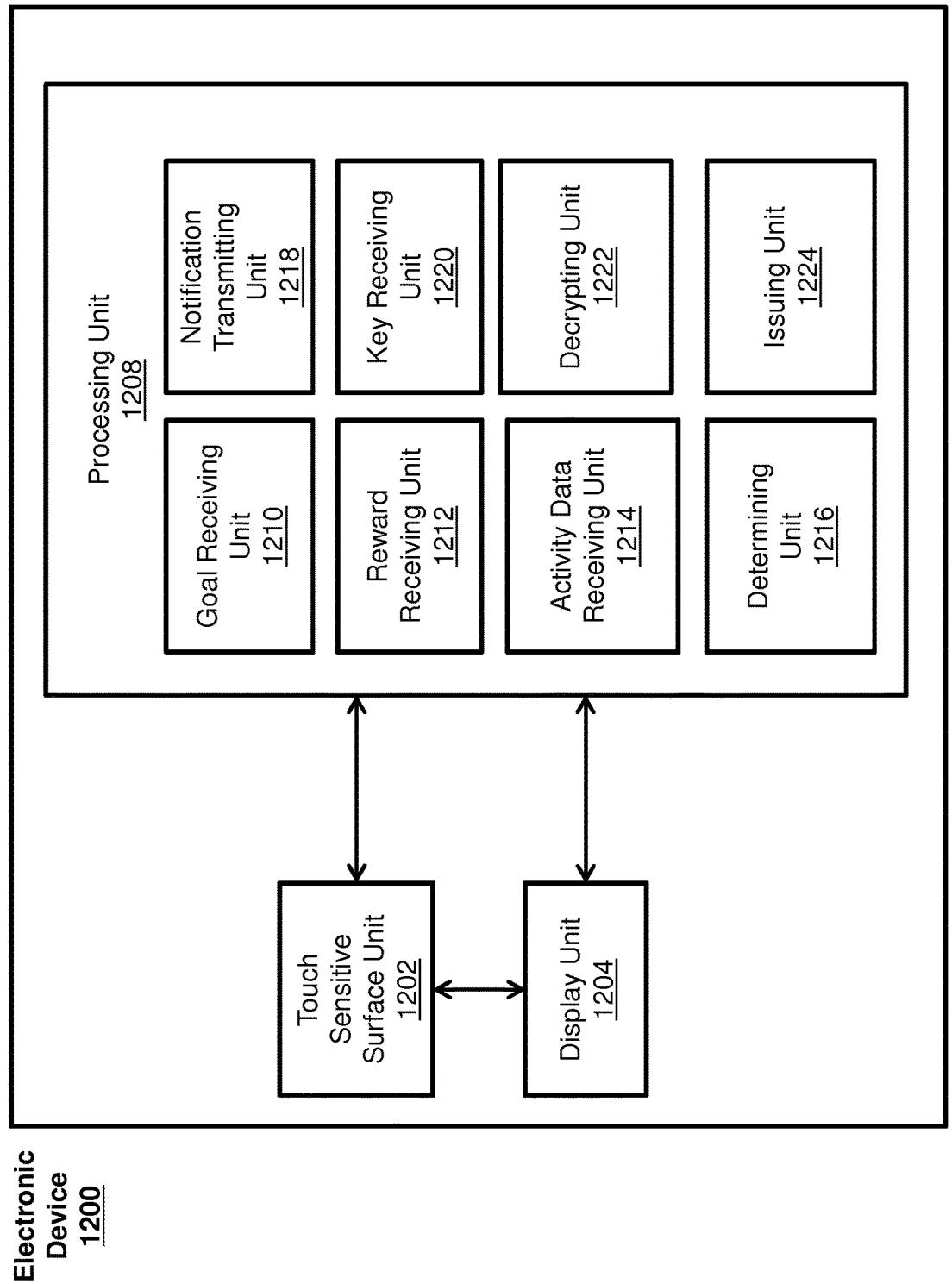
FIG. 12 illustrate functional block diagrams of electronic devices configured to provide rewards to users for physical activity tracked using an electronic device according to various examples.

In accordance with some examples, FIG. 12 shows a functional block diagram of an electronic device 1200 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 12 can be combined or separated into sub-blocks to implement the principles of the various described examples. Therefore, the description herein optionally supports any possible combination or separation or further definition of the functional blocks described herein.

As shown in FIG. 12, electronic device 1200 can include a display unit 1204 configured to display graphical objects, a touch-sensitive surface unit 1202 configured to receive user gestures, and a processing unit 1208. In some examples, processing unit 1208 can include goal receiving unit 1210, reward receiving unit 1212, activity data receiving unit 1214, determining unit 1216, notification transmitting unit 1218, key receiving unit 1220, decrypting unit 1222, and issuing unit 1224.

Processing unit 1208 can be configured to receive (e.g., using goal receiving unit 1210) a physical activity goal to be completed by a user associated with the electronic device. Reward receiving unit 1212 can be configured to receive an encrypted reward that is to be given to the user in response to the user completing the physical activity goal. Activity data receiving unit 1214 can be configured to receive activity data generated by an activity sensor of the electronic device, wherein the activity data is representative of movement associated with the electronic device that is detected by the activity sensor. Determining unit 1216 can be configured to determine, based on the activity data, whether the user has completed the physical activity goal. Notification transmitting unit 1218 can be configured to transmit a notification that the user has completed the physical activity goal to one or more servers. Key receiving unit 1220 can be configured to receive, from the one or more servers, a key for decrypting the encrypted reward. Decrypting unit 1222 can be configured to decrypt the encrypted reward using the key.

In some examples, the physical activity goal includes: an amount of physical activity to be performed by the user; and a duration during which the amount of physical activity is to be performed by the user. In some examples, determining, based on the activity data, whether the user has completed the physical activity goal includes: determining an aggregate amount of physical activity performed by the user based on the activity data; determining whether the aggregate amount of physical activity performed by the user is greater than or equal to the amount of physical activity to be performed by the user; and determining whether the duration during which the amount of physical activity is to be performed by the user has elapsed. In some examples, determining that the user has completed the physical activity goal includes: determining that the aggregate amount of the physical activity performed by the user is greater than or equal to the amount of physical activity to be performed by the user; and determining that the duration during which the amount of physical activity is to be performed by the user has not elapsed.

In some examples, the amount of physical activity to be performed by the user includes a number of Calories to expend, a distance to travel, or a number of steps to be taken.

In some examples, the physical activity goal includes: a location to be traveled to by the user; and a duration during which the location is to be traveled to by the user. In some examples, determining, based on the activity data, whether the user has completed the physical activity goal includes: determining a location of the electronic device based on the activity data; determining whether the location of the electronic device is within a threshold distance from the location to be traveled to by the user; and determining whether the duration during which the location is to be traveled to by the user has elapsed.

In some examples, determining that the user has completed the physical activity goal includes: determining that the location of the electronic device is within the threshold distance from the location to be traveled to by the user; and determining that the duration during which the location is to be traveled to by the user has not elapsed.

In some examples, the reward includes an image, a video, a song, an audio message, an electronic text document, or an amount of virtual currency.

In some examples, issuing unit 1224 can be configured to issue the reward to the user by allowing access to the image, the video, the song, or the text document.

In some examples, device 1200 is a wearable electronic device.

Figure 13:
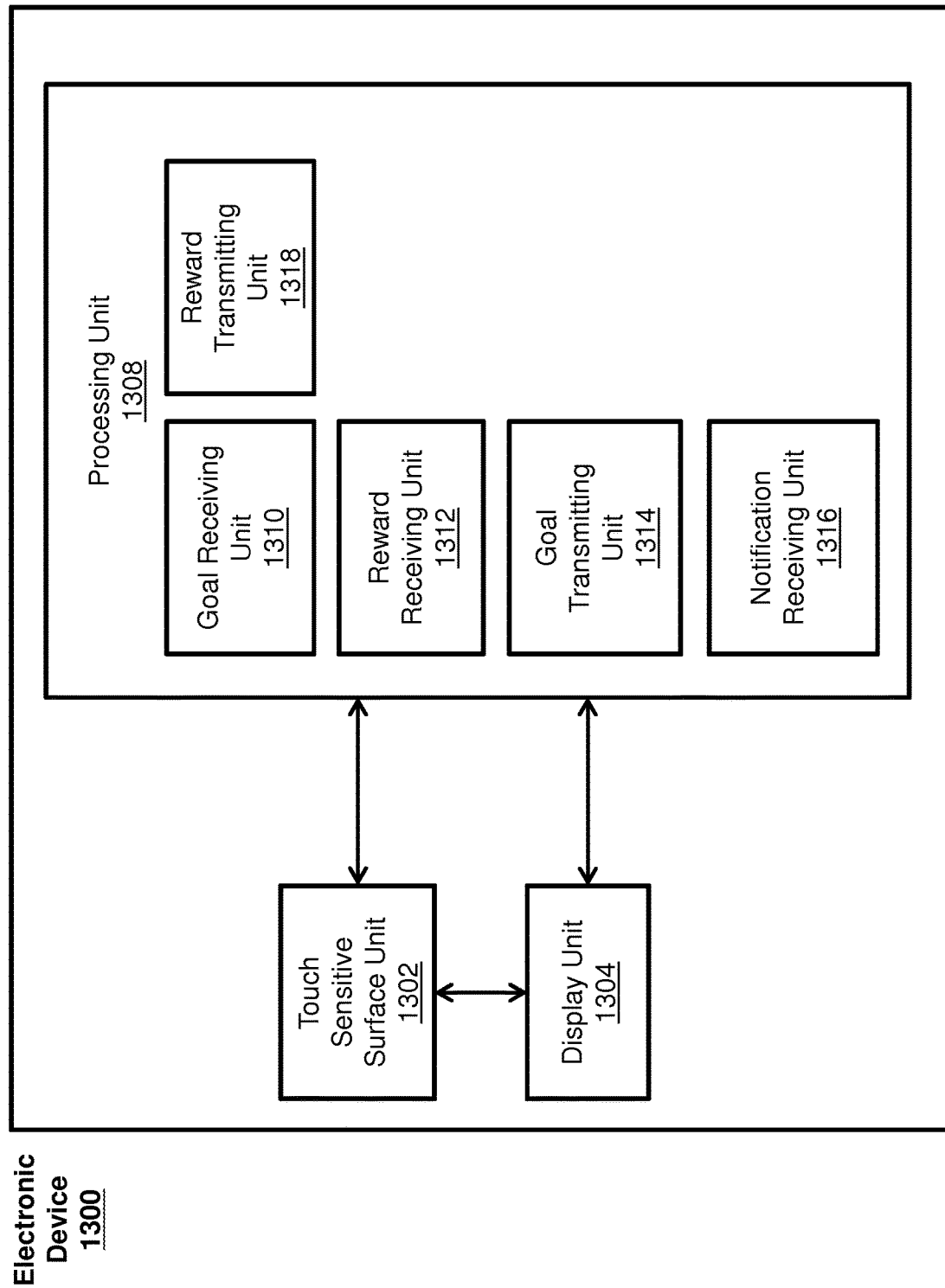
FIG. 13 illustrate functional block diagrams of electronic devices configured to provide rewards to users for physical activity tracked using an electronic device according to various examples.

In accordance with some examples, FIG. 13 shows a functional block diagram of an electronic device 1300 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 13 can be combined or separated into sub-blocks to implement the principles of the various described examples. Therefore, the description herein optionally supports any possible combination or separation or further definition of the functional blocks described herein.

As shown in FIG. 13, electronic device 1300 can include a display unit 1304 configured to display graphical objects, a touch-sensitive surface unit 1302 configured to receive user gestures, and a processing unit 1308. In some examples, processing unit 1308 can include goal receiving unit 1310, reward receiving unit 1312, goal transmitting unit 1314, notification receiving unit 1316, and reward transmitting unit 1318.

Processing unit 1308 can be configured to receive (e.g., using goal receiving unit 1310), from a first user device, a physical activity goal to be completed by a user associated with a second user device. Reward receiving unit 1312 can be configured to receive, from the first user device, a reward that is to be given to the user in response to the user completing the physical activity goal. Goal transmitting unit 1314 can be configured to transmit the physical activity goal to the second user device. Notification receiving unit 1316 can be configured to receive, from the second user device, a notification that the user completed the physical activity goal. Reward transmitting unit 1318 can be configured to transmit, in response to receiving the notification, the reward to the second user device.

In some examples, the physical activity goal includes: an amount of physical activity to be performed by the user; and a duration during which the amount of physical activity is to be performed by the user.

In some examples, the amount of physical activity to be performed by the user includes a number of Calories to expend, a distance to travel, or a number of steps to be taken.

In some examples, the physical activity goal includes: a location to be traveled to by the user; and a duration during which the location is to be traveled to by the user.

In some examples, the reward includes an image, a video, a song, an audio message, an electronic text document, or an amount of virtual currency.

Figure 14:
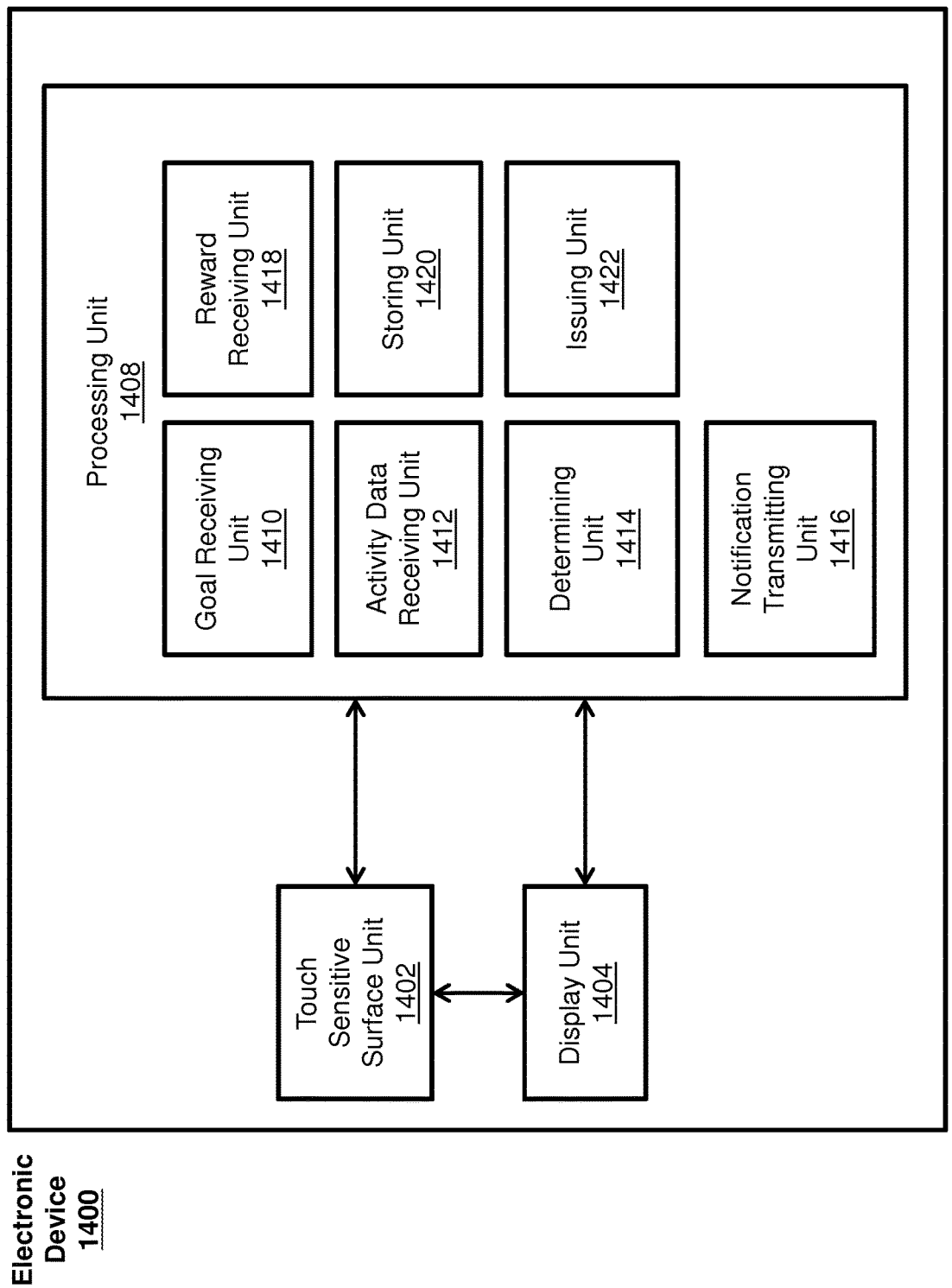
FIG. 14 illustrate functional block diagrams of electronic devices configured to provide rewards to users for physical activity tracked using an electronic device according to various examples.

In accordance with some examples, FIG. 14 shows a functional block diagram of an electronic device 1400 configured in accordance with the principles of the various described examples. The functional blocks of the device can be implemented by hardware, software, or a combination of hardware and software to carry out the principles of the various described examples. It is understood by persons of skill in the art that the functional blocks described in FIG. 14 can be combined or separated into sub-blocks to implement the principles of the various described examples. Therefore, the description herein optionally supports any possible combination or separation or further definition of the functional blocks described herein.

As shown in FIG. 14, electronic device 1400 can include a display unit 1404 configured to display graphical objects, a touch-sensitive surface unit 1402 configured to receive user gestures, and a processing unit 1408. In some examples, processing unit 1408 can include goal receiving unit 1410, activity data receiving unit 1412, determining unit 1414, notification transmitting unit 1416, reward receiving unit 1418, storing unit 1420, and issuing unit 1422.

Processing unit 1408 can be configured to receive (e.g., using goal receiving unit 1410) a physical activity goal to be completed by a user associated with the electronic device. Activity data receiving unit 1412 can be configured to receive activity data generated by an activity sensor of the electronic device, wherein the activity data is representative of movement associated with the electronic device that is detected by the activity sensor. Determining unit 1414 can be configured to determine, based on the activity data, whether the user has completed the physical activity goal. Notification transmitting unit 1416 can be configured to transmit, in accordance with a determination that the user has completed the physical activity goal, a notification that the user has completed the physical activity goal to one or more servers. Reward receiving unit 1418 can be configured to receive, in accordance with a determination that the user has completed the physical activity goal, a reward that is to be given to the user in response to the user completing the physical activity goal. Storing unit 1420 can be configured to store, in accordance with a determination that the user has completed the physical activity goal, the reward in a released state, wherein access to the reward is allowed while in the released state.

In some examples, the physical activity goal includes: an amount of physical activity to be performed by the user; and a duration during which the amount of physical activity is to be performed by the user.

In some examples, determining, based on the activity data, whether the user has completed the physical activity goal includes: determining an aggregate amount of physical activity performed by the user based on the activity data; determining whether the aggregate amount of physical activity performed by the user is greater than or equal to the amount of physical activity to be performed by the user; and determining whether the duration during which the amount of physical activity is to be performed by the user has elapsed.

In some examples, determining that the user has completed the physical activity goal includes: determining that the aggregate amount of the physical activity performed by the user is greater than or equal to the amount of physical activity to be performed by the user; and determining that the duration during which the amount of physical activity is to be performed by the user has not elapsed.

In some examples, the amount of physical activity to be performed by the user includes a number of Calories to expend, a distance to travel, or a number of steps to be taken.

In some examples, the physical activity goal includes: a location to be traveled to by the user; and a duration during which the location is to be traveled to by the user.

In some examples, determining, based on the activity data, whether the user has completed the physical activity goal includes: determining a location of the electronic device based on the activity data; determining whether the location of the electronic device is within a threshold distance from the location to be traveled to by the user; and determining whether the duration during which the location is to be traveled to by the user has elapsed.

In some examples, determining that the user has completed the physical activity goal includes: determining that the location of the electronic device is within the threshold distance from the location to be traveled to by the user; and determining that the duration during which the location is to be traveled to by the user has not elapsed.

In some examples, the reward includes an image, a video, a song, an audio message, an electronic text document, or an amount of virtual currency.

In some examples, issuing unit 1422 can be configured to issue the reward to the user by allowing access to the image, the video, the song, or the text document.

In some examples, the device 1400 is a wearable electronic device.

As described above, one aspect of the present technology is the gathering and use of data available from various sources to improve the delivery to users of invitational content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, home addresses, or any other identifying information.

The present disclosure recognizes that the use of such personal information data, in the present technology, can be used to the benefit of users. For example, the personal information data can be used to deliver targeted content that is of greater interest to the user. Accordingly, use of such personal information data enables calculated control of the delivered content. Further, other uses for personal information data that benefit the user are also contemplated by the present disclosure.

The present disclosure further contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. For example, personal information from users should be collected for legitimate and reasonable uses of the entity and not shared or sold outside of those legitimate uses. Further, such collection should occur only after receiving the informed consent of the users. Additionally, such entities would take any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of advertisement delivery services, the present technology can be configured to allow users to select to "opt in" or "opt out" of participation in the collection of personal information data during registration for services. In another example, users can select not to provide location information for targeted content delivery services. In yet another example, users can select to not provide precise location information, but permit the transfer of location zone information.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, content can be selected and delivered to users by inferring preferences based on non-personal information data or a bare minimum amount of personal information, such as the content being requested by the device associated with a user, other non-personal information available to the content delivery services, or publically available information.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the appended claims.

What is claimed is:

1. A computer-implemented method, comprising:
   receiving, by an electronic device, a communication comprising a physical activity goal challenge including a physical activity goal;
   receiving activity data generated by an activity sensor of the electronic device, the activity data being representative of user movement associated with the electronic device that is detected by the activity sensor;
   determining, based on the activity data, whether the physical activity goal has been completed; and
   in response to determining that the physical activity goal has been completed: transmitting, to one or more servers, a notification that the physical activity goal has been completed;
   receiving a reward from the one or more servers; and
   storing the reward in a released state, access to the reward being allowed while in the released state.

2. The computer-implemented method of claim 1, further comprising:
   accessing the reward in the released state; and
   presenting the reward using an output device of the electronic device after accessing the reward.

3. The computer-implemented method of claim 1, wherein:
   the electronic device is associated with a first user; and
   receiving the communication comprising the physical activity goal comprises receiving, by the electronic device from another electronic device associated with a second user, data representing the physical activity goal.

4. The computer-implemented method of claim 1, wherein receiving the communication comprising the physical activity goal comprises receiving the communication comprising receiving, at the electronic device, user input representing the physical activity goal.

5. The computer-implemented method of claim 1, wherein the received reward is encrypted, wherein the method further comprises, in accordance with a determination that the physical activity goal has been completed:
   receiving, from the one or more servers, a key; and
   decrypting the encrypted reward using the key.

6. The computer-implemented method of claim 1, wherein determining, based on the activity data, whether the physical activity goal has been completed comprises:
   determining an aggregate amount of physical activity performed based on the activity data;
   determining whether the aggregate amount of physical activity performed is greater than or equal to an amount of physical activity to be performed; and
   determining whether a duration during which the amount of physical activity is to be performed has elapsed.

7. The computer-implemented method of claim 1, wherein determining, based on the activity data, whether the physical activity goal has been completed comprises:
   determining that an aggregate amount of the physical activity performed is greater than or equal to an amount of physical activity to be performed; and
   determining that a duration during which the amount of physical activity is to be performed has not elapsed.

8. The computer-implemented method of claim 1, wherein the physical activity goal comprises:
   a location to be traveled to; and
   a duration during which the location is to be traveled to.

9. A computer-readable storage medium storing computer-executable instructions that, when executed by one or more processors of an electronic device, cause the electronic device to perform operations comprising:
   receiving, by the electronic device, a communication comprising a physical activity goal challenge including a physical activity goal;
   receiving activity data generated by an activity sensor of the electronic device, the activity data being representative of user movement associated with the electronic device that is detected by the activity sensor;
   determining, based on the activity data, whether the physical activity goal has been completed; and
   in response to determining that the physical activity goal has been completed:
   transmitting, to one or more servers, a notification that the physical activity goal has been completed;
   receiving a reward from the one or more servers; and
   storing the reward in a released state, access to the reward being allowed while in the released state.

10. The computer-readable storage medium of claim 9, wherein:
    the electronic device is associated with a first user; and
    receiving the communication comprising the physical activity goal comprises receiving, by the electronic device from another electronic device associated with a second user, data representing the physical activity goal.

11. The computer-readable storage medium of claim 9, wherein receiving the communication comprising the physical activity goal comprises receiving the communication comprising receiving, at the electronic device, user input representing the physical activity goal.

12. The computer-readable storage medium of claim 9, wherein the received reward is encrypted, wherein the computer-readable storage medium comprises additional computer-executable instructions that, when executed by the one or more processors, cause the electronic device to perform additional operations comprising, in accordance with a determination that the physical activity goal has been completed:
    receiving, from the one or more servers, a key; and
    decrypting the encrypted reward using the key.

13. The computer-readable storage medium of claim 9, wherein determining, based on the activity data, whether the physical activity goal has been completed comprises:
    determining an aggregate amount of physical activity performed based on the activity data;
    determining whether the aggregate amount of physical activity performed is greater than or equal to an amount of physical activity to be performed; and
    determining whether a duration during which the amount of physical activity is to be performed has elapsed.

14. The computer-readable storage medium of claim 9, wherein determining, based on the activity data, whether the physical activity goal has been completed comprises:
    determining that an aggregate amount of the physical activity performed is greater than or equal to an amount of physical activity to be performed; and
    determining that a duration during which the amount of physical activity is to be performed has not elapsed.

15. The computer-readable storage medium of claim 9, wherein the physical activity goal comprises:
    a location to be traveled to; and
    a duration during which the location is to be traveled to.

16. A mobile device, comprising:
an activity sensor; and
one or more processors in communication with one or more memories and the activity sensor, the one or more processors configured to execute computer-executable instructions stored on the one or more memories to at least:
receive a communication comprising a physical activity goal challenge including a physical activity goal;
receive activity data generated by the activity sensor, the activity data being representative of user movement associated with the mobile device that is detected by the activity sensor;
determine, based on the activity data, whether the physical activity goal has been completed; and
in response to determining that the physical activity goal has been completed:
transmit, to one or more servers, a notification that the physical activity goal has been completed;
receive a reward from the one or more servers; and
store the reward in a released state, access to the reward being allowed while in the released state.

17. The mobile device of claim 16, wherein:
the mobile device is associated with a first user; and
receiving the communication comprising the physical activity goal comprises receiving, from another electronic device associated with a second user, data representing the physical activity goal.

18. The mobile device of claim 16, wherein receiving the communication comprising the physical activity goal comprises receiving the communication comprising receiving user input representing the physical activity goal.

19. The mobile device of claim 16, wherein the received reward is encrypted, and wherein the one or more processors are further configured to execute further computer-executable instructions stored on the one or more memories to at least, in accordance with a determination that the physical activity goal has been completed:
receiving, from the one or more servers, a key; and
decrypting the encrypted reward using the key.

20. The mobile device of claim 16, wherein determining, based on the activity data, whether the physical activity goal has been completed comprises:
determining an aggregate amount of physical activity performed based on the activity data;
determining whether the aggregate amount of physical activity performed is greater than or equal to an amount of physical activity to be performed; and
determining whether a duration during which the amount of physical activity is to be performed has elapsed.

* * * * *